United States Patent
Ebi et al.

(10) Patent No.: US 9,046,505 B2
(45) Date of Patent: Jun. 2, 2015

(54) SAMPLE PREPARATION APPARATUS

(75) Inventors: Ryuichiro Ebi, Osaka (JP); Koki Tajima, Kobe (JP)

(73) Assignee: Sysmex Corporation, Hyogo (JP)

( * ) Notice: Subject to any disclaimer, the term of this patent is extended or adjusted under 35 U.S.C. 154(b) by 0 days.

(21) Appl. No.: 13/010,623

(22) Filed: Jan. 20, 2011

(65) Prior Publication Data

US 2011/0176976 A1 Jul. 21, 2011

(30) Foreign Application Priority Data

Jan. 21, 2010 (JP) ................................. 2010-011241
Oct. 29, 2010 (JP) ................................. 2010-243693

(51) Int. Cl.

| B01F 11/02 | (2006.01) |
|---|---|
| G01N 35/04 | (2006.01) |
| B01F 3/12 | (2006.01) |
| G01N 15/14 | (2006.01) |
| B01F 3/00 | (2006.01) |
| G01N 1/40 | (2006.01) |

(52) U.S. Cl.
CPC .............. *G01N 35/04* (2013.01); *B01F 3/1242* (2013.01); *B01F 11/0266* (2013.01); *B01F 2003/0042* (2013.01); *G01N 2001/4094* (2013.01); *G01N 15/14* (2013.01); *G01N 2015/149* (2013.01)

(58) Field of Classification Search
None
See application file for complete search history.

(56) References Cited

U.S. PATENT DOCUMENTS

| 2,405,849 A * | 8/1946 | Riker ................................. 4/680 |
| 2,815,193 A * | 12/1957 | Brown ........................... 366/113 |
| 3,198,489 A * | 8/1965 | Finch ............................. 366/113 |
| 5,328,826 A | 7/1994 | Nozawa et al. |
| 5,603,342 A | 2/1997 | Shambaugh |
| 5,736,100 A | 4/1998 | Miyake et al. |
| 6,420,003 B2 * | 7/2002 | Shaw et al. ................... 428/35.9 |
| 2002/0002767 A1 | 1/2002 | Yanagita |
| 2002/0009015 A1 * | 1/2002 | Laugharn et al. ............. 366/108 |
| 2003/0166260 A1 * | 9/2003 | Katou et al. ................. 435/287.1 |
| 2005/0004091 A1 * | 1/2005 | Albeck et al. ................. 514/183 |
| 2005/0221399 A1 | 10/2005 | Nakano et al. |
| 2008/0308404 A1 | 12/2008 | Luotola et al. |

(Continued)

FOREIGN PATENT DOCUMENTS

| EP | 2 261 632 A1 | 12/2010 |
| JP | 5-80053 A | 3/1993 |

(Continued)

OTHER PUBLICATIONS

A.M. Loske et al., "Bactericidal effect of underwater shock waves on *Escerichia coli* ATCC 10536 suspensions", 2002, Innovative Food Science & Emerging Technologies, 3: 321-327.*

(Continued)

*Primary Examiner* — Jill Warden
*Assistant Examiner* — Timothy G Kingan
(74) *Attorney, Agent, or Firm* — Sughrue Mion, PLLC

(57) ABSTRACT

A sample preparation apparatus, comprising: an ultrasonic vibrating unit which applies ultrasonic vibration to a sample including an analyte held in a measurement sample container; a sample preparation unit which prepares a measurement sample by mixing the sample including the analyte to which the ultrasonic vibration is applied and a predetermined reagent; and a container transporting unit which transports the measurement sample container holding the sample including the analyte from the ultrasonic vibrating unit to the sample preparation unit.

21 Claims, 20 Drawing Sheets

(56) References Cited

U.S. PATENT DOCUMENTS

2008/0312581 A1 * 12/2008 Hardy .............................. 604/22
2011/0014685 A1    1/2011 Fukuda et al.

FOREIGN PATENT DOCUMENTS

| | | |
|---|---|---|
| JP | 8-146007 | 6/1996 |
| JP | 10-505427 A | 5/1998 |
| JP | 10-229066 | 8/1998 |
| JP | 2966057 B | 10/1999 |
| JP | 2000/084508 | 3/2000 |
| JP | 2003/254981 A | 9/2003 |
| JP | 2004/037187 | 2/2004 |
| JP | 2005-315862 A | 11/2005 |
| JP | 2006-189384 A | 7/2006 |
| JP | 2006/242806 | 9/2006 |
| JP | 2008/541069 A | 11/2008 |
| WO | 2009/123000 A1 | 8/2009 |

OTHER PUBLICATIONS

G.L. Garcia and W.E. Tolles, Ultrasonic disaggregation of cell clusters, 1977, Journal of Histochemistry and Cytochemistry, 25(7): 508-512.*

* cited by examiner

SAMPLE PREPARATION APPARATUS

FIELD OF THE INVENTION

The present invention relates to a sample preparation apparatus.

BACKGROUND

As a cell analyzer for analyzing cells contained in a biological sample collected from a living body, a cell analyzer for measuring epithelial cells of the uterine cervix contained a sample collected from the uterine cervix of a subject by a flow cytometer and screening cancer and atypical cells is conventionally known (e.g. European Patent publication No. EP2261632).

In the cell analyzer described in European Patent publication No. EP2261632, the cancer and atypical cells are stained with a fluorescent marker for specifically staining the cancer and atypical cells and a fluorescence generated from the cancer and atypical cells is measured with a flow cytometer.

When the cells to be stained are mutually aggregated in staining the cells, the screening accuracy of the cancer and atypical cells may be reduced. However, a technique to separate such aggregated cells automatically has not been known.

SUMMARY

The scope of the present invention is defined solely by the appended claims, and is not affected to any degree by the statements within this summary.

A first aspect of the present invention is a sample preparation apparatus, comprising: an ultrasonic vibrating unit which applies ultrasonic vibration to a sample including an analyte held in a measurement sample container; a sample preparation unit which prepares a measurement sample by mixing the sample including the analyte to which the ultrasonic vibration is applied and a predetermined reagent; and a container transporting unit which transports the measurement sample container holding the sample including the analyte from the ultrasonic vibrating unit to the sample preparation unit.

DETAILED DESCRIPTION OF THE EMBODIMENT

The embodiments of the sample preparation apparatus of the present invention will be described in detail below with reference to the accompanying drawings.

The sample preparation apparatus of the present invention can be used in the cell analyzer which analyzes cells collected from patients. First, the cell analyzer will be described.

[Overall Configuration of the Cell Analyzer]

Figure 1:
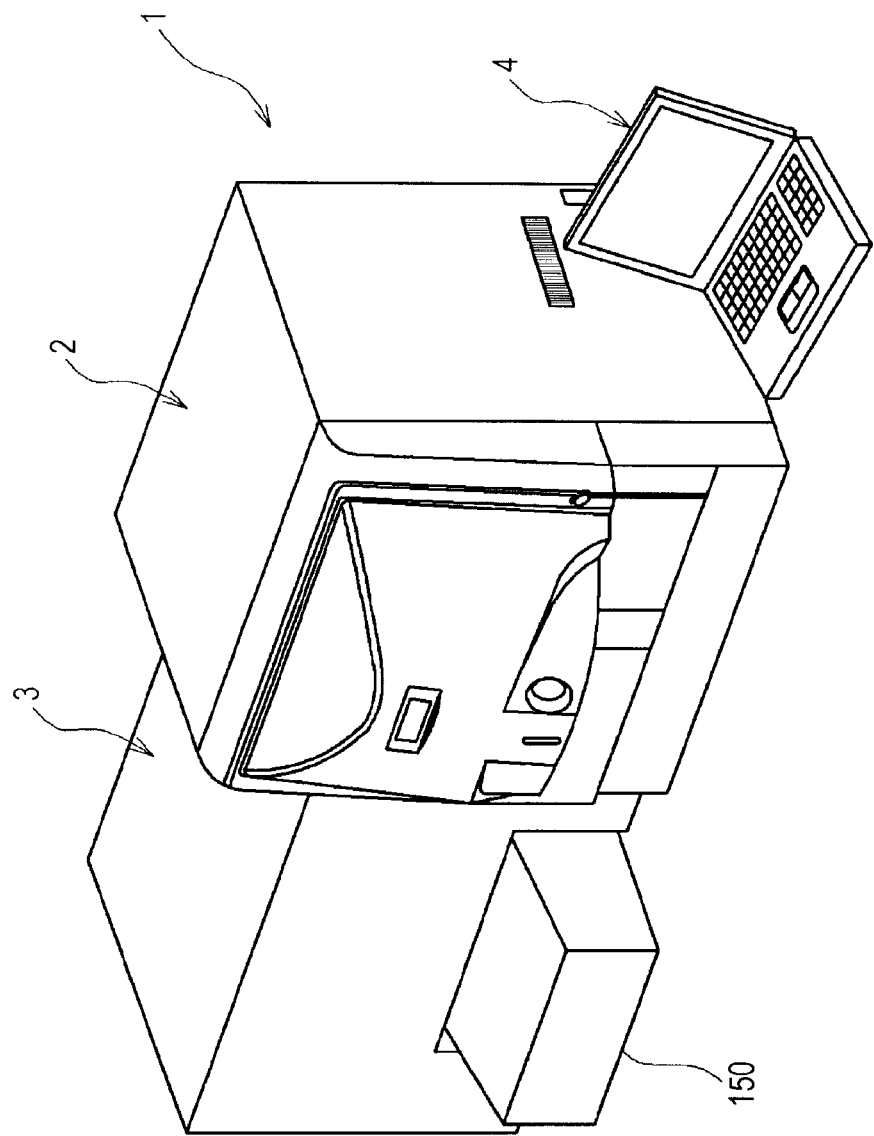
FIG. 1 is a perspective view of a cell analyzer having a sample preparation apparatus according to one embodiment of the present invention.

FIG. 1 is a perspective view of a cell analyzer 1 having a sample preparation apparatus according to one embodiment of the present invention.

The cell analyzer 1 is used for determining whether or not cancer cells are contained in the cells by flowing a measurement sample containing the cells collected from the patients into a flow cell, irradiating the measurement sample flowing through the flow cell with a laser beam, detecting light from the measurement sample (scattered light or fluorescence (e.g. forward scattered light and lateral fluorescence)), and analyzing the light signals thereof.

More specifically, the cell analyzer 1 of the present embodiment is intended to analyze epithelial cells of the uterine cervix and used for screening uterine cervix carcinoma.

As shown in FIG. 1, the cell analyzer 1 includes a measurement apparatus 2 which performs optical measurement with a laser beam on the measurement sample, a sample preparation apparatus 3 which produces the measurement sample to be supplied to the measurement apparatus 2 by subjecting a biological sample collected from a subject to pretreatments such as cleaning and staining, and a data processing apparatus 4 which analyzes the measured results in the measurement apparatus 2.

A main constituent element of the cell analyzer 1 will be sequentially described.

[Internal Configuration of the Measurement Apparatus]

Figure 2:
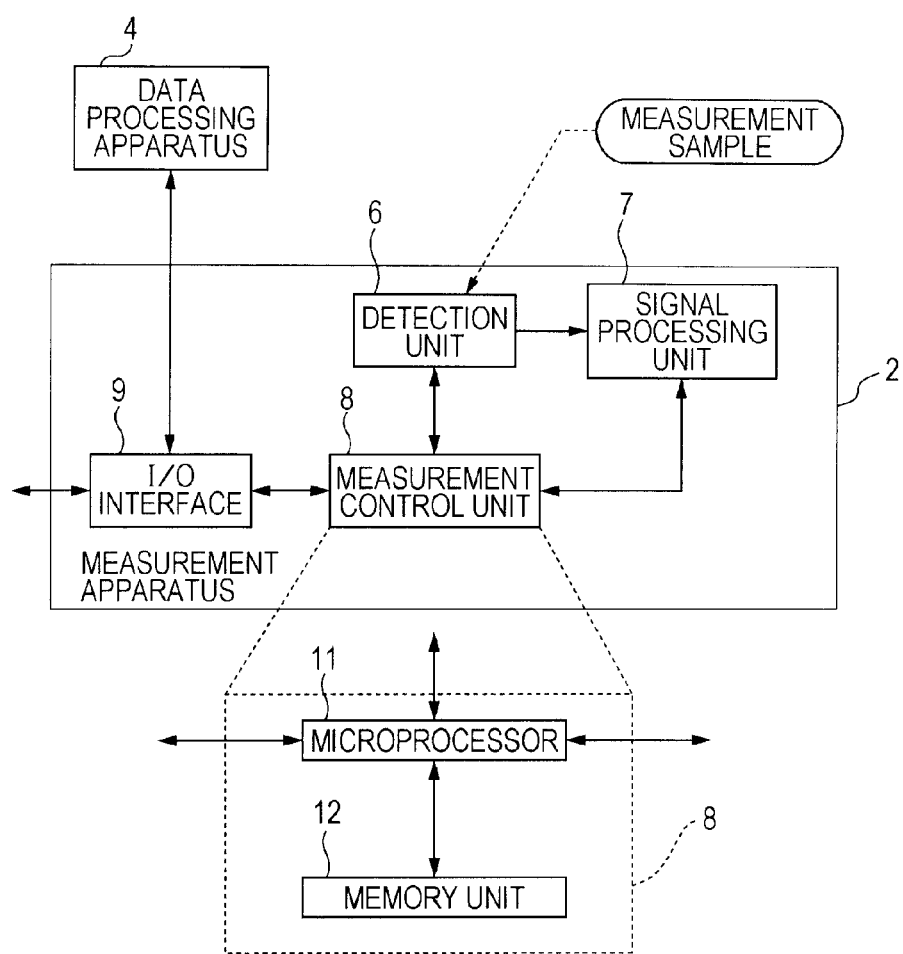
FIG. 2 is a block diagram showing an internal configuration of a measurement apparatus.

FIG. 2 is a block diagram showing an internal configuration of a measurement apparatus 2.

As shown in FIG. 2, the measurement apparatus 2 includes a detection unit 6, a signal processing unit 7, a measurement control unit 8, and an I/O interface 9.

Figure 9:
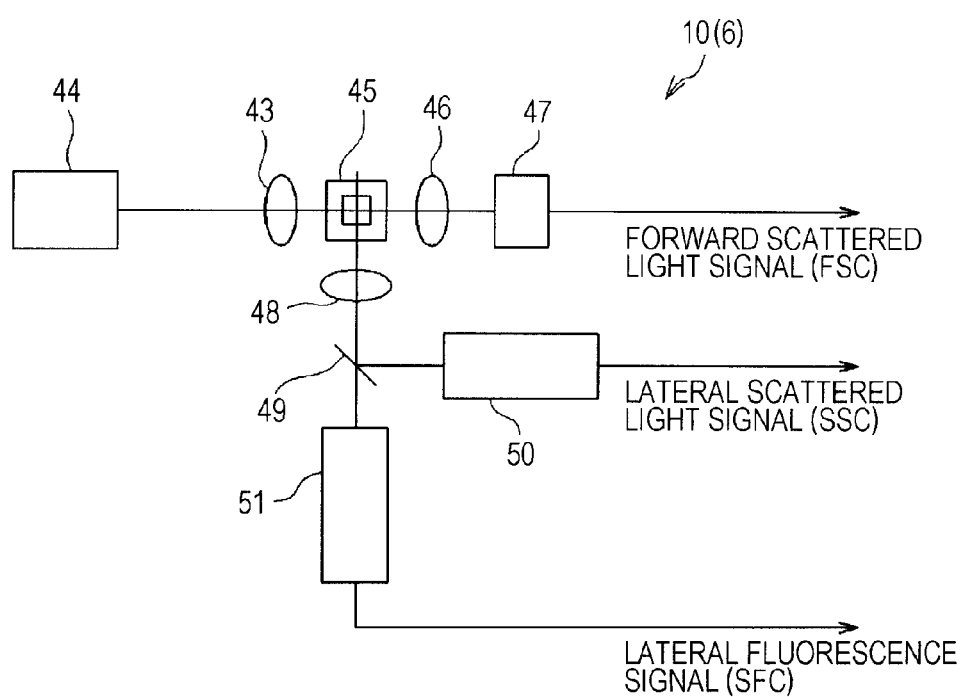
FIG. 9 is a functional block diagram of a flow cytometer which includes a detection unit.
Figure 10:
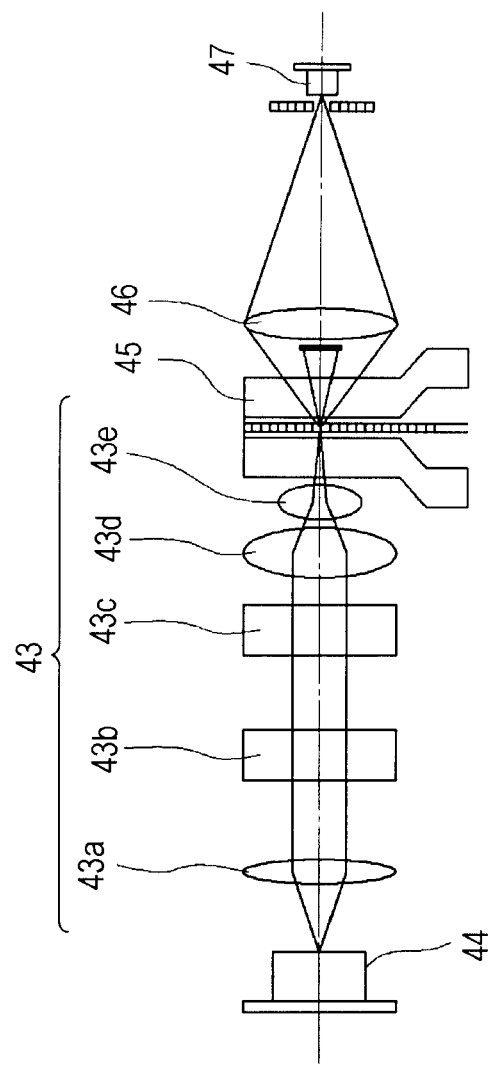
FIG. 10 is a side view showing an optical system of the flow cytometer.

Among them, the detection unit 6 detects cells to be measured and the number and size of nuclei in the cells from the measurement sample. In the present embodiment, a flow cytometer 10 shown in FIGS. 9 and 10 is employed as the detection unit 6.

The signal processing unit 7 includes a signal processing circuit which performs a required signal process on an output signal from the detection unit 6. The measurement control unit 8 includes a microprocessor 11 and a memory unit 12, and the memory unit 12 includes a ROM, a RAM, and the like.

Control programs which perform operation control of the detection unit 6 or the signal processing unit 7 as well as data required for executing the control programs are stored in the ROM of the memory unit 12. The microprocessor 11 is capable of executing the control programs by loading the control programs stored in the ROM in the RAM or directly executing the control programs from the ROM.

The microprocessor 11 of the measurement control unit 8 is connected to the data processing apparatus 4 and a microprocessor 19 of a preparation control unit 16 to be described later through the I/O interface 9. Thus, the microprocessor 11 can transmit and receive data processed by the microprocessor itself or data required for the microprocessor's own process with the data processing apparatus 4 and the microprocessor 19 of the preparation control unit 16.

[Configuration of the Sample Preparation Apparatus]

Figure 3:
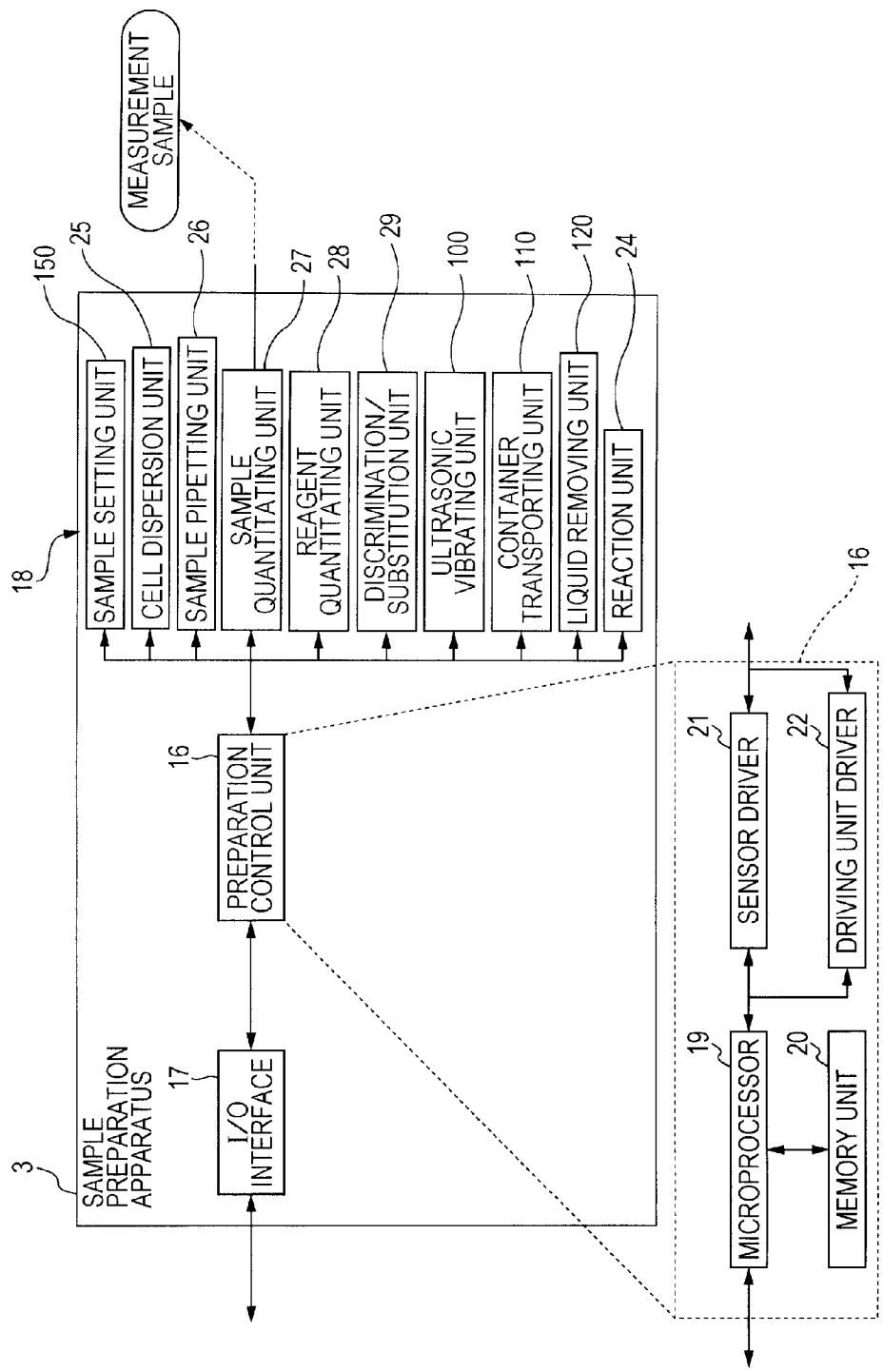
FIG. 3 is a block diagram showing an internal configuration of the sample preparation apparatus.

FIG. 3 is a block diagram showing an internal configuration of the sample preparation apparatus 3.

As shown in FIG. 3, the sample preparation apparatus 3 includes the preparation control unit 16, an I/O interface 17, and a preparation device unit 18 which automatically adjusts components of the biological sample.

The preparation control unit 16 includes the microprocessor 19, a memory unit 20, a sensor driver 21, and a driving unit driver 22. The memory unit 20 includes a ROM, a RAM, and the like.

The preparation device unit 18 of the present embodiment is configured by a sample setting unit 150, a cell dispersing unit 25, a sample pipetting unit 26, a sample quantitating unit 27, a reagent quantitating unit 28, a discrimination/substitution unit 29, an ultrasonic vibrating unit 100, a container transporting unit 110, a liquid removing unit 120, and a reaction unit 24.

Figure 11:
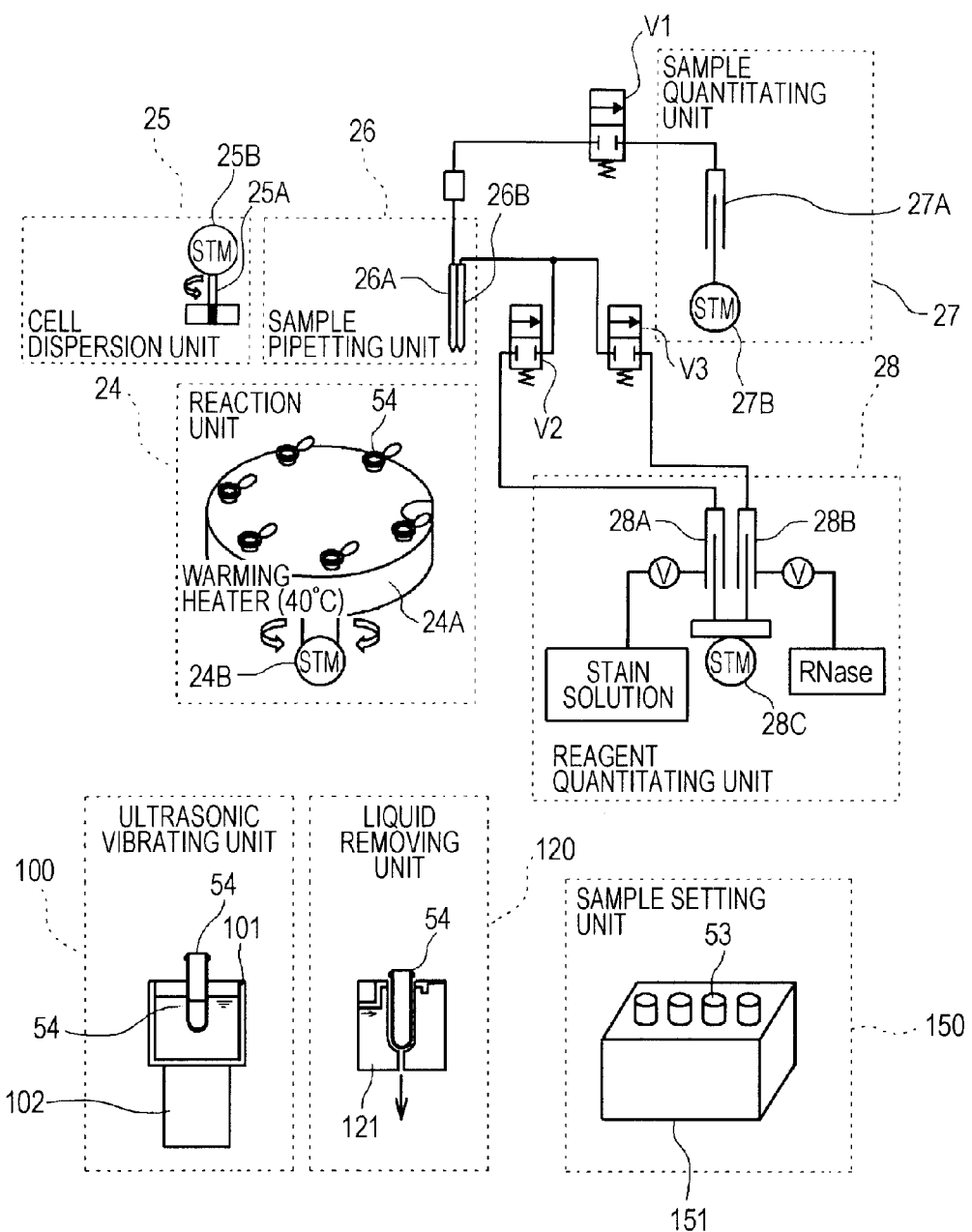
FIG. 11 is a fluid circuit diagram of the preparation device unit.

Among them, the sample setting unit 150 is provided to set a plurality of biological sample containers 53 which hold biological samples collected from the patients and a preservative solution containing methanol as a main ingredient (see FIG. 11). The reaction unit 24 is provided to set the measurement sample container 54 which holds the prepared liquid sample (see FIG. 11).

The cell dispersing unit 25 forcedly disperses cells contained in the sample by stirring a mixed solution of the biological samples and the preservative solution.

The sample pipetting unit (sample dispensing unit) 26 introduces the mixed solution of the biological samples containing the dispersed cells and the preservative solution retrieved from the biological sample containers 53 into the fluid circuit of the preparation device unit 18, and retrieves a prepared liquid sample discharged to the measurement sample containers 54 (see FIG. 11) from the measurement sample containers 54. The sample quantitating unit 27 quantifies the mixed solution of the biological samples and the preservative solution to be supplied to the fluid circuit. The reagent quantitating unit 28 quantifies a reagent such as a stain solution to be added to the biological samples.

The discrimination/substitution unit 29 is provided to substitute the preservative solution with a diluted solution and discriminate cells to be measured from the other cells (red blood cells, white blood cells, etc.) or bacteria. The discrimination/substitution unit 29 is provided to obtain a liquid sample in which the concentration of the cells to be measured is increased from the liquid sample containing the discriminated and substituted cells to be measured.

The ultrasonic vibrating unit 100 is provided to apply ultrasonic vibration to the measurement sample whose concentration is improved in the discrimination/substitution unit 29 to separate the aggregated cells to be measured.

The container transporting unit 110 is provided to grip the measurement sample container 54 (see FIG. 4) installed in the reaction unit 24 and transport the measurement sample container 54 among the reaction unit 24, the container mounting part 130, the ultrasonic vibrating unit 110, and the liquid removing units 120.

The liquid removing unit 120 is provided to remove a solution portion attached to the outer periphery surface of the measurement sample container 54 immersed in the liquid (see FIG. 6) in the ultrasonic vibrating unit 100. The removal of the solution portion can prevent the measurement sample container 54 from adhering to the reaction unit 24 when the measurement sample container 54 is arranged in the reaction unit 24 and left for a long time.

The configuration of the fluid circuit of the preparation device unit 18 having respective units 24 to 29, 100, 110, 120, and 150 (FIGS. 11 and 12) will be described later.

Control programs which perform operation control of the sensor driver 21 and the driving unit driver 22 as well as data required for executing the control programs are stored in the ROM of the memory unit 20. The microprocessor 19 is capable of executing the control programs loaded in the RAM or directly executing the control programs in the ROM.

The microprocessor 19 of the preparation control unit 16 is connected to the microprocessor 11 of the measurement control unit 8 through the I/O interface 17. Thus, the microprocessor 19 can transmit and receive data processed by the microprocessor itself or data required for the microprocessor's own process with the microprocessor 11 of the measurement control unit 8.

The microprocessor 19 of the preparation control unit 16 is connected to sensors of respective units 24 to 29, 100, 110, 120, and 150 in the preparation device unit 18 and a driving motor configured by the driving unit through the sensor driver 21 and a driving unit driver 22, executes the control programs based on detection signals from the sensors, and controls the operation of the driving unit.

The sample preparation apparatus 3 according to the present embodiment performs a process for separating the cells to be measured which are aggregated in the liquid sample by applying ultrasonic vibration to the condensed liquid sample containing the cells to be measured in the discrimination/substitution unit 29 as described later.

Figure 4:
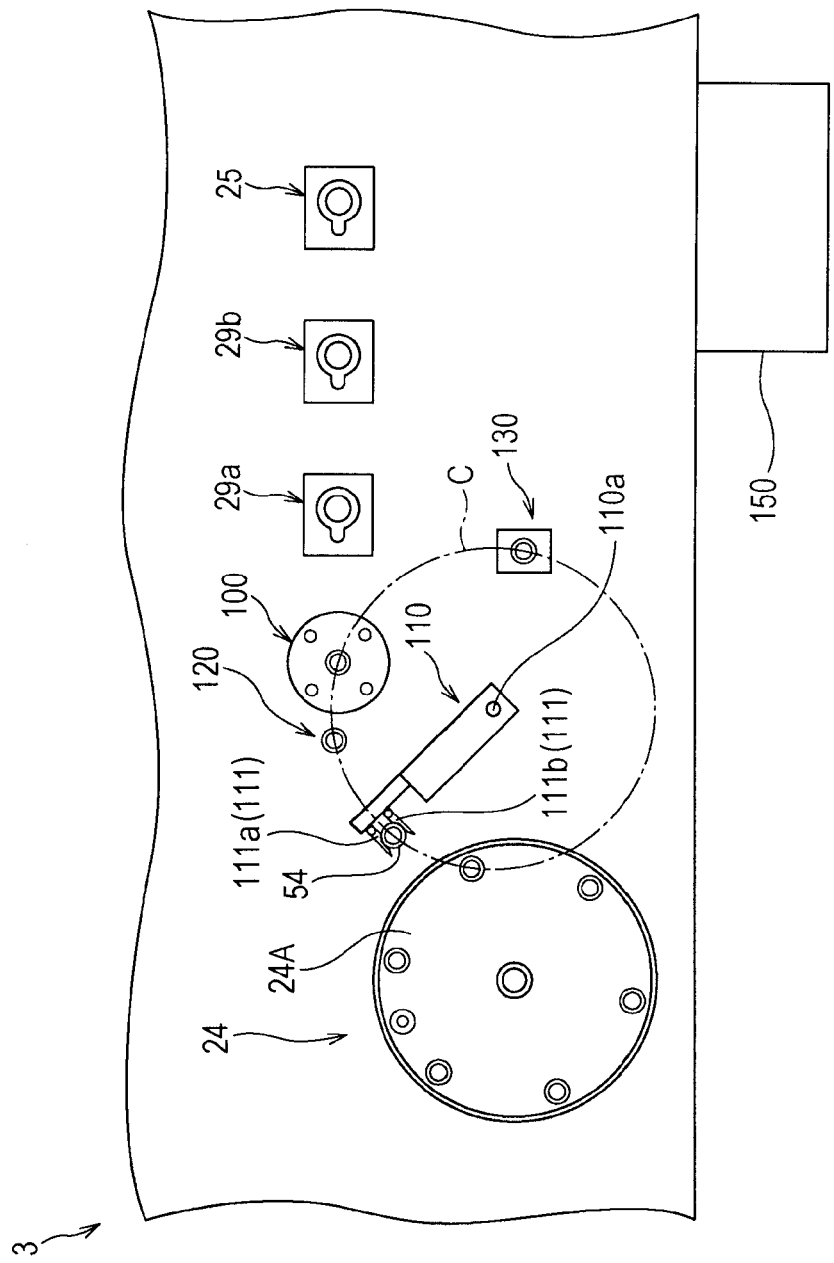
FIG. 4 is a plane explanatory view of the sample preparation apparatus.

FIG. 4 is a plane explanatory view of an element of the sample preparation apparatus 3 according to such an ultrasonic process. For the ultrasonic process, the sample preparation apparatus 3 includes the ultrasonic vibrating unit 100, the container transporting unit 110, the liquid removing unit 120, and the container mounting part 130. The ultrasonic vibrating unit 100, liquid removing unit 120, and container mounting part 130 are arranged on the same circumference. One of six positions for arranging the measurement sample container in the reaction unit 24 can be arranged on the circumference. Specifically, the ultrasonic vibrating unit 100 is arranged on the circumference centering on the rotation center of the container transporting unit 110. Therefore, the measurement sample container 54 can be transported among the ultrasonic vibrating unit 100, the liquid removing unit 120, the container mounting part 130, and the reaction unit 24 by rotating the container transporting unit 110.

Figure 5:
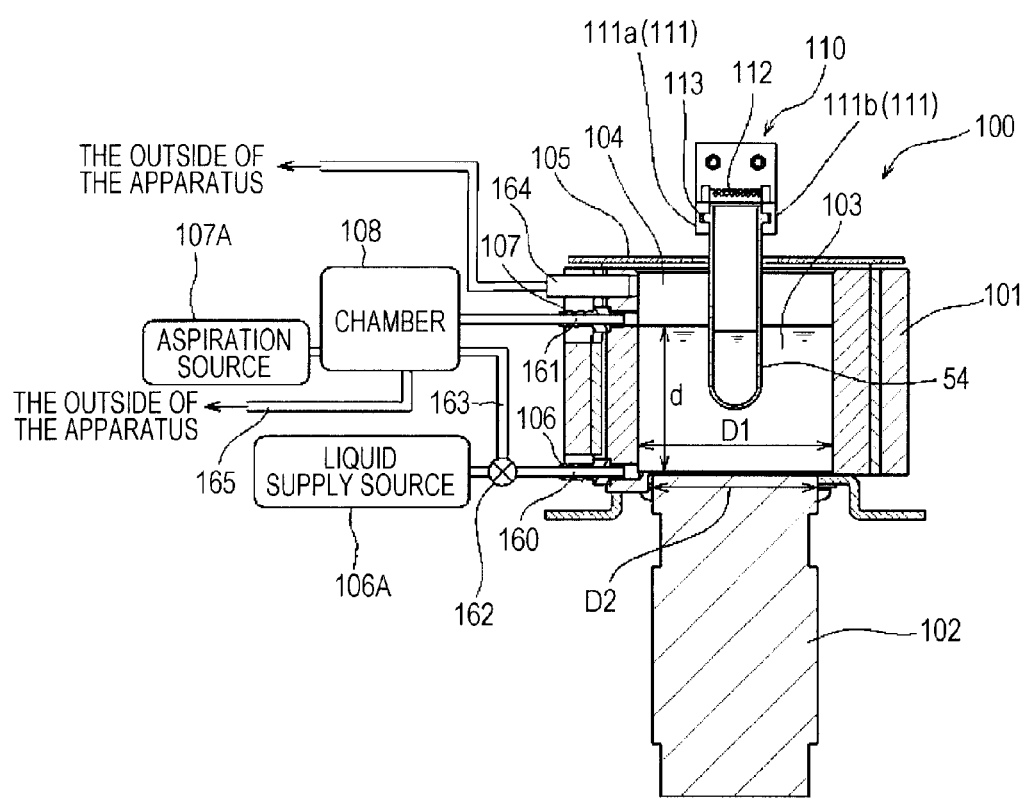
FIG. 5 is a cross sectional explanatory view of an ultrasonic vibrating unit.

The ultrasonic vibrating unit 100 includes a liquid holding part 101 and an ultrasonic transducer 102 as shown in FIG. 5. The liquid holding part 101 with a cylindrical body shape has a concave portion 104 which holds a liquid 103 such as water. A lid 105 in which a circular hole having a size capable of inserting the measurement sample container 54 is formed is provided on an opening of the concave portion 104. The lid 105 can prevent the liquid 103 from scattering to the outside by ultrasonic vibration.

The ultrasonic transducer 102 with a cylindrical shape is arranged at the lower part of the liquid holding part 101. Thus, it is not necessary to waterproof the ultrasonic transducer 102 and the configuration can be simplified. As the ultrasonic transducer 102, for example, known ultrasonic transducers used for cleaning parts can be used.

A supply hole 106 which supplies the liquid 103 from a liquid supply source 106A to the concave portion 104 of the liquid holding part 101 is formed at the lower part of the peripheral wall of the liquid holding part 101. On the other hand, a discharge hole 107 which discharges the liquid 103 from the concave portion 104 by an aspiration source 107A is formed at the upper part of the peripheral wall. The supply hole 106 and the liquid supply source 106A are connected by a duct 160, and the discharge hole and a chamber 108 are connected by a duct 161. A flow channel switching valve 162 is arranged in the middle of the duct 160, and the flow channel switching valve 162 and the chamber 108 are connected by a duct 163. The drive of the liquid supply source 106A and the aspiration source 107A is controlled by the preparation control unit 16 of the sample preparation apparatus 3.

An overflow channel 164 for preventing the liquid 103 from overflowing from the concave portion 104 of the liquid holding part 101 is formed on the peripheral wall of the liquid holding part 101 and at the further upper part of the discharge hole 107. The overflow channel 164 is connected the outside of the apparatus.

As well as the aspiration source 107A, the duct 161, and the duct 163, a discharge pipe 165 which discharges the liquid 103 introduced into the chamber 108 by the aspiration source 107A to the outside of the apparatus is connected to the chamber 108.

The flow channel switching valve 162 allows the liquid supply source 106A to communicate with the concave portion 104 when supplying the liquid 103 to the concave portion 104 of the liquid holding part 101, while the valve is switched so as to allow the chamber 108 to communicate with the concave portion 104 when discharging the liquid 103 from the concave portion 104 of the liquid holding part 101.

In order to generate ultrasonic vibration effectively, a depth d (depth of the liquid with the measurement sample container 54 immersed) is set so that a node of the ultrasonic waves generated by the ultrasonic transducer 102 is positioned on the surface of the liquid 103 held in the concave portion 104.

In the present embodiment, the measurement sample container 54 is immersed in the liquid in the concave portion 104 of the liquid holding part 101, then a predetermined amount of liquid is supplied from the supply hole 106 to the concave portion 104, the aspiration source is driven by the preparation control unit 16 for a predetermined time, and an excessive amount of the liquid 103 in the concave portion 104 is discharged from the discharge hole 107. The height from the bottom surface of the concave portion 104 to the lower end of the discharge hole 107 is set so that the node of the ultrasonic waves generated by the ultrasonic transducer 102 is positioned on the surface of the liquid 103. Thus, when the liquid in the concave portion 104 is continuously aspirated for a predetermined time, the position of the surface of the liquid 103 is controlled so as to be the position of the node of the ultrasonic waves. The "predetermined time" for aspirating the liquid can be set to a time obtained by adding a time of about several seconds to the time calculated from the amount of the supplied liquid and the discharge capability of the aspiration source. Even when aspirating for a longer time than the time to be calculated, the liquid at the lower side than the discharge hole 107 is not discharged, which causes no trouble in controlling the liquid surface.

An inner diameter D1 of the liquid holding part 101 with a tubular shape is larger by about several mm, for example, about 5 to 6 mm than an outer diameter D2 of the ultrasonic transducer 102 with a cylindrical shape. The ultrasonic vibration can be efficiently transmitted to the liquid by making the size of the liquid portion to which ultrasonic waves are applied larger than that of the ultrasonic transducer 102.

The measurement sample container 54 is immersed in the liquid of the liquid holding part 101 (see FIG. 5) with the measurement sample container gripped by a gripping part 111 with a scissors-like shape of the container transporting unit 110. At that time, a lowered position of the container transporting unit 110 is set so that the surface of the liquid sample in the measurement sample container 54 is positioned at the lower side than the surface of the liquid 103 in the concave portion 104. When the surface of the liquid sample in the measurement sample container 54 is positioned at the upper side than the surface of the liquid 103 in the concave portion 104, the ultrasonic vibration cannot be effectively transmitted to the liquid sample. As a result, the aggregated cells to be measured in the liquid sample cannot be reliably separated. In the present invention, the position of the liquid surface is not particularly limited, and the surface of the liquid sample in the measurement sample container 54 is preferably positioned at the lower side by about 1 to 2 mm than the surface of the liquid 103 in the concave portion 104.

The measurement sample container 54 can be made with a synthetic resin or metal such as stainless steel, and it is preferably made with a material having an acoustic impedance equivalent to an acoustic impedance of the liquid held in the concave portion 104. For example, when water is held in the concave portion 104, the measurement sample container 54 is preferably made with synthetic resins such as polypropylene and polyethylene. In the present embodiment, the ultrasonic vibration is indirectly applied to the liquid sample through the liquid in the concave portion 104, but the transmission efficiency of the ultrasonic vibration can be improved by making characteristics (acoustic impedance) of the liquid which transmits the ultrasonic vibration equivalent to those of the measurement sample container 54.

The inner periphery surface of the measurement sample container 54 has preferably a certain amount of roughness from the viewpoint of improving dispersion effects. Specifically, it is preferable to set the surface roughness to, for example, about 1 to 30 μm.

The frequency of the ultrasonic vibration applied by the ultrasonic transducer 102 is not particularly limited in the present invention, and it is preferably 20 kHz or more, further preferably from 20 to 75 kHz.

As shown in FIG. 4, the container transporting unit 110 is arranged so that a rotation center 110a is positioned in the center of the ultrasonic vibrating unit 100, the liquid removing unit 120, and a circle C formed by the container mounting part 130. The gripping part 111 with a scissors-like shape is provided on the distal end of the container transporting unit 110. As shown in FIG. 5, the gripping part 111 with a scissors-like shape includes a matched pair of gripping pieces 111a and 111b, and both the gripping pieces 111a and 111b are biased toward the close direction by a spring 112. Grooves 113 which engage with flanges 54a having a circular shape formed at the upper end of the measurement sample container 54 (see FIG. 6) are formed on surfaces facing each of the gripping pieces 111a and 111b.

Returning to FIG. 4, the transportation of the measurement sample container 54 by the container transporting unit 110 is performed as follows.

Figure 6:
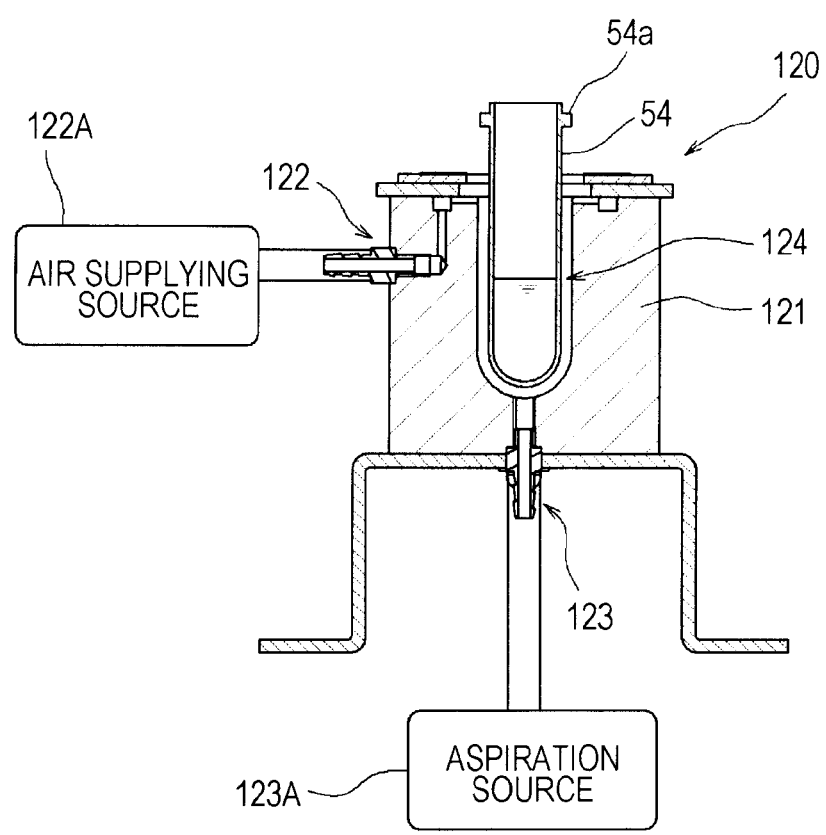
FIG. 6 is a cross sectional explanatory view of a liquid removing unit.

First, the container transporting unit 110 is rotated to engage both the gripping pieces 111a and 111b of the gripping part 111 with the flanges 54a having a circular shape formed at the upper end of the measurement sample container 54 (see FIG. 6). In this case, the gripping part 111 is gripping the measurement sample container 54 with a bias force of the spring 112.

Then, the container transporting unit 110 is raised and rotated up to the position to which the measurement sample container 54 is moved. Thereafter, the container transporting unit 110 is lowered and both the gripping pieces 111a and 111b of the gripping part 111 are opened while resisting the bias force of the spring 112. Thus, the engagement of the grooves 113 of the gripping pieces 111a and 111b with the flanges 54a of the measurement sample container 54 is released and the measurement sample container 54 is arranged at a predetermined position.

As shown in FIG. 6, the liquid removing unit 120 includes a body 121, an air supplying unit 122, and an air aspirating unit 123. The body 121 has a holding concave portion 124 which can hold at least portion immersed in the liquid in the concave portion 104 in the measurement sample container 54. The horizontal section of the holding concave portion 124 has a round shape and the inner diameter is larger by about several mm than the outer diameter of the measurement sample container 54, so that some space between the outer periphery surface of the measurement sample container 54 inserted into the holding concave portion 124 and the outer periphery surface of the holding concave portion 124 can be secured.

Figure 7:
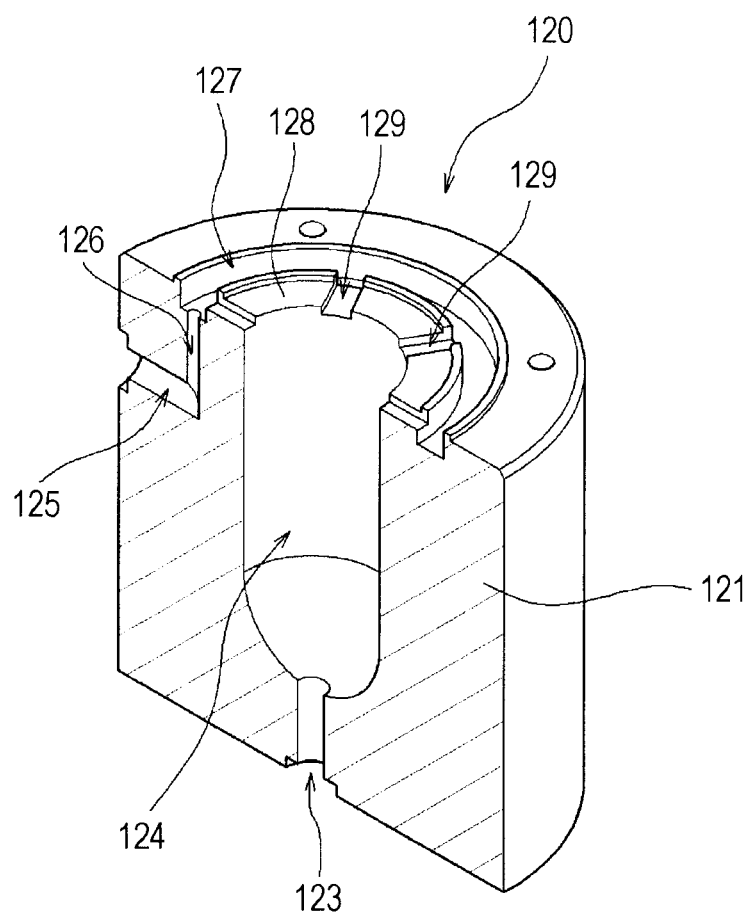
FIG. 7 is a perspective explanatory view of the peripheral edge of an opening of the liquid removing unit.

The air supplying unit 122 is provided near the upper part of the body 121 so as to supply air to the outer periphery surface of the measurement sample container 54 held in the holding concave portion 124. The air supplying unit 122 is connected to an air supplying source (positive pressure applying source) 122A and includes a horizontal air supplying passage 125, a vertical air supplying passage 126, a circular air supplying passage 127, and an air supplying opening 129 as shown in FIG. 7. Six of the air supplying opening 129 are formed on a projecting wall 128 arranged along the peripheral edge of the opening of the holding concave portion 124 in a circumferential direction at regular intervals.

On the other hand, as shown in FIG. 6, the air aspirating unit 123 is provided on the bottom of the holding concave portion 124 and it is connected to the aspiration source 123A.

As shown in FIG. 7, air supplied from the air supplying source 122A is passed through the horizontal air supplying passage 125, the vertical air supplying passage 126, the circular air supplying passage 127, and the air supplying opening 129 and is sprayed on the outer periphery surface of the measurement sample container 54 held in the holding concave portion 124. The liquid attached to the outer periphery surface of the measurement sample container 54 is blown away from the outer periphery surface by the sprayed air and is discharged together with the air from the air aspirating unit 123.

[Internal Configuration of the Data Processing Unit]

Figure 8:
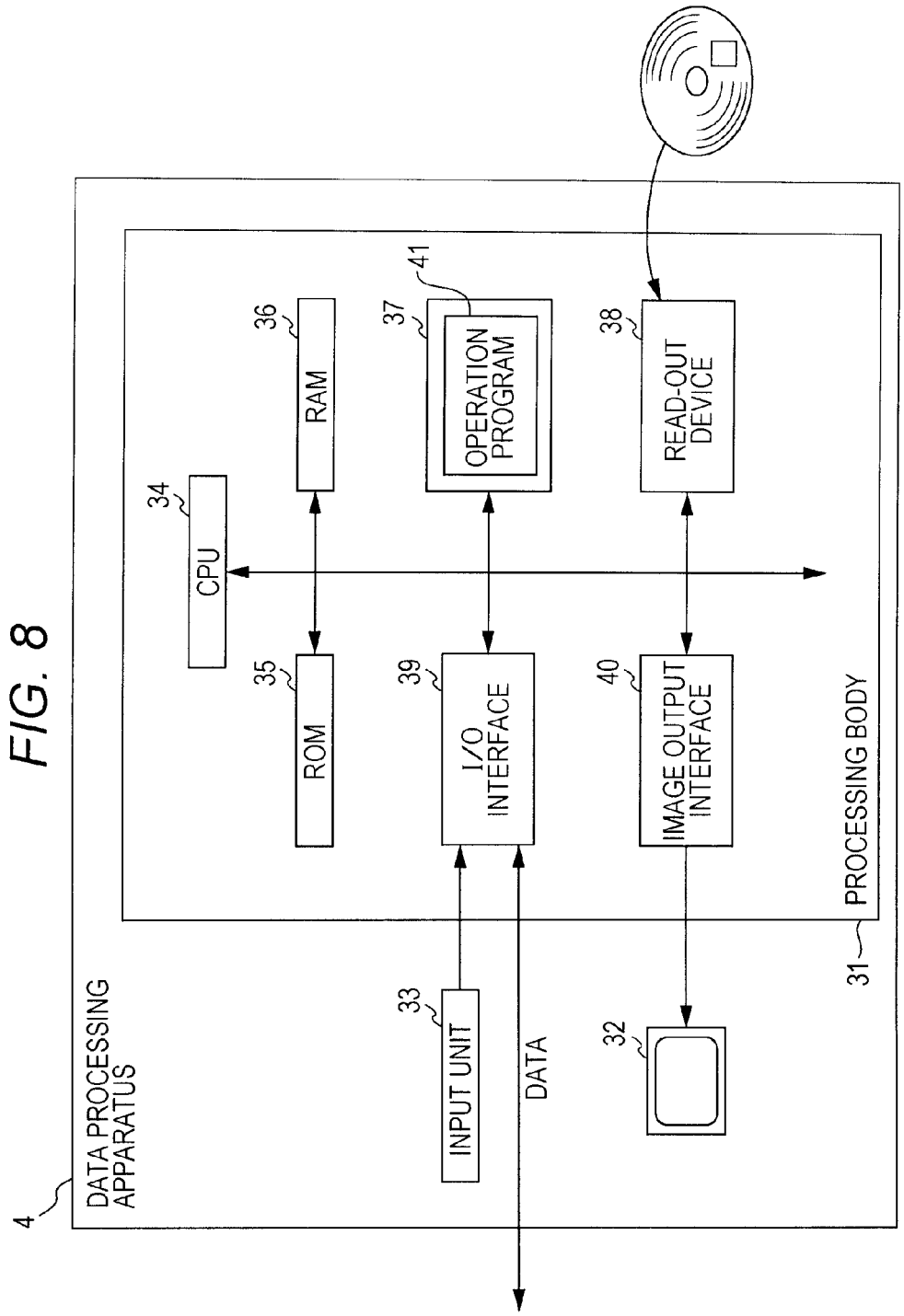
FIG. 8 is a block diagram showing an internal configuration of a data processing apparatus.

FIG. 8 is a block diagram showing an internal configuration of a data processing apparatus 4.

As shown in FIG. 8, the data processing apparatus 4 of the present embodiment is configured by a personal computer, for example, a notebook PC (a desktop type PC may be used.) and mainly includes a processing body 31, a display 32, and an input unit 33.

The processing body 31 includes a CPU34, a ROM35, a RAM36, a hard disk 37, a read-out device 38, an I/O interface 39, and an image output interface 40. The respective units are communicably connected by an internal bus.

The CPU34 is capable of executing the computer programs stored in the ROM35 and the computer programs loaded in the RAM36.

The ROM35 is configured by a mask ROM, a PROM, an EPROM, an EEPROM, and the like. The computer programs to be executed by CPU34 and data to be used for the computer programs are stored in the ROM35.

The RAM36 is configured by a SRAM, a DRAM, and the like, and is used to read out various computer programs recorded on the ROM35 and the hard disk 37 or is used as a work region of the CPU34 when executing the computer programs.

Various computer programs to be executed by the CPU34 such as operating system and application program, as well as data used in executing the programs are installed in the hard disk 37.

An operating system providing a graphical user interface environment such as Windows (registered trademark) manufactured and sold by US Microsoft Co. is installed in the hard disc 37.

An operation program 41 which performs transmission of operation instructions to the measurement control unit 8 and the preparation control unit 16, processes of receiving and analyzing measured results performed by the measurement apparatus 2, and display of processed analysis results is installed in the hard disc 37. The operation program 41 is assumed to operate on the operating system.

The read-out device 38 is configured by a flexible disk drive, a CD-ROM drive or a DVD-ROM drive. The read-out device 38 is capable of reading out computer programs or data recorded in a portable recording medium.

The I/O interface 39 is configured by serial interfaces such as USB, IEEE 1394, and RS-232C, parallel interfaces such as SCSI, IDE, and IEEE 1284, and an analog interface including D/A and ND converters.

The I/O interface 39 is connected to the input device 33 including a keyboard and a mouse. The user can input data to the computer using the input unit 33.

The I/O interface 39 is also connected to the I/O interface 9 of the measurement apparatus 2 described above, so that the measurement apparatus 2 can transmit and receive data with the data processing apparatus 4.

The image output interface 40 is connected to the display 32 including a LCD or a CRT and allows the display 32 to output an image signal corresponding to the image data from the CPU34.

[Configuration of the Detection Unit (Flow Cytometer)]

FIG. 9 is a functional block diagram of the flow cytometer 10 which includes the detection unit 6. FIG. 10 is a side view showing an optical system of the flow cytometer 10.

As shown in FIG. 9, a lens system 43 of the flow cytometer 10 focuses the laser beam from a semiconductor laser 44 which is a light source on the measurement sample flowing through a flow cell 45. A light collecting lens 46 focuses the forward scattered light of the cells in the measurement sample on a scattered light detector including a photodiode 47.

The lens system 43 is illustrated as a single lens in FIG. 9. Specifically, it has, for example, a configuration shown in FIG. 10.

That is, the lens system 43 of the present embodiment is configured by a collimator lens 43*a*, a cylindrical lens system (a planoconvex cylindrical lens 43*b*+a biconcave cylindrical lens 43*c*), and a condenser lens system (a condenser lens 43*d*+a condenser lens 43*e*) in this order from the side of the semiconductor laser 44 (the left-hand side of FIG. 10).

Returning to FIG. 9, a lateral light collecting lens 48 focuses the lateral scattered light and lateral fluorescence of cells to be measured or nuclei in the cells on a dichroic mirror 49. The dichroic mirror 49 reflects the lateral scattered light on a photomultiplier 50 which is a scattered light detector and transmits the lateral fluorescence to a photomultiplier 51 which is a fluorescence detector. These lights reflect features of the cells and nuclei in the measurement sample.

The photodiode 47 and each of the photomultipliers 50 and 51 convert received light signals into electric signals and output a forward scattered light signal (FSC), a lateral scattered light signal (SSC), and a lateral fluorescence signal (SFL), respectively. These output signals are amplified by a preamplifier (not shown) and sent to the signal processing unit 7 (see FIG. 2) of the measurement apparatus 2.

Each of the signals FSC, SSC, and SFL processed by the signal processing unit 7 of the measurement apparatus 2 is transmitted to the data processing apparatus 4 from the I/O interface 9 by the microprocessor 11 (see FIG. 8).

The CPU34 of the data processing apparatus 4 creates a scattergram for analyzing the cells and nuclei from each of the signals FSC, SSC, and SFL by executing the operation program 41 and determines whether or not the cells in the measurement sample are abnormal cells, specifically cancerous cells based on the scattergram.

As a light source of the flow cytometer 10, a gas laser can also be used in place of the semiconductor laser 44, and the semiconductor laser 44 is preferably employed from the viewpoint of low cost, small size, and low power. Reduction of product cost as well as miniaturization and electric power saving of the apparatus are achieved by using the semiconductor laser 44.

In the present embodiment, a blue semiconductor laser with a short wavelength which has an advantage in narrowing the beam is used. The blue semiconductor laser is also effective for a fluorescence excitation wavelength such as PI. Among the semiconductor lasers, a red semiconductor laser having advantages of low cost, a long life, and the stable supply from manufacturers may be used.

An average size of epithelial cells of the uterine cervix is about 60 μm. The size of nuclei of the epithelial cells is from 5 to 7 μm. When the cells become cancerous, the frequency of cell division is abnormally increased and the size of nuclei becomes from 10 to 15 μm. Thus, a N/C ratio (size of nuclei/size of cells) is higher than that of normal cells.

Therefore, there is provided an index for determining whether or not the cells become cancerous by detecting the size of cells and nuclei.

In the present embodiment, the photodiode 47 detects the scattered light from the measurement sample flowing through the flow cell 45 and the photomultiplier 51 detects the fluorescence from the measurement sample flowing through the flow cell 45.

The signal processing unit 7 of the measurement apparatus 2 (see FIG. 2) acquires a pulse width of the scattered light signal which is a value reflecting the size of the cells to be measured from the scattered light signal output from the photodiode 47 and acquires a pulse width of the fluorescence signal which is a value reflecting the size of nuclei of the cells to be measured from the fluorescence signal output from the photomultiplier 51.

The CPU34 of the data processing apparatus 4 which includes an analyzing unit is configured to determine whether or not the cells to be measured are abnormal cells based on the value reflecting the size of the cells to be measured acquired by the signal processing unit 7 and the value reflecting the size of nuclei of the cells to be measured.

Specifically, the CPU34 of the data processing apparatus 4 determines that the cells to be measured are abnormal cells when the peak, nuclear diameter, and area values of the cells to be measured are larger than a predetermined threshold.

[Fluid Circuit of the Preparation Device Unit]

Figure 12:
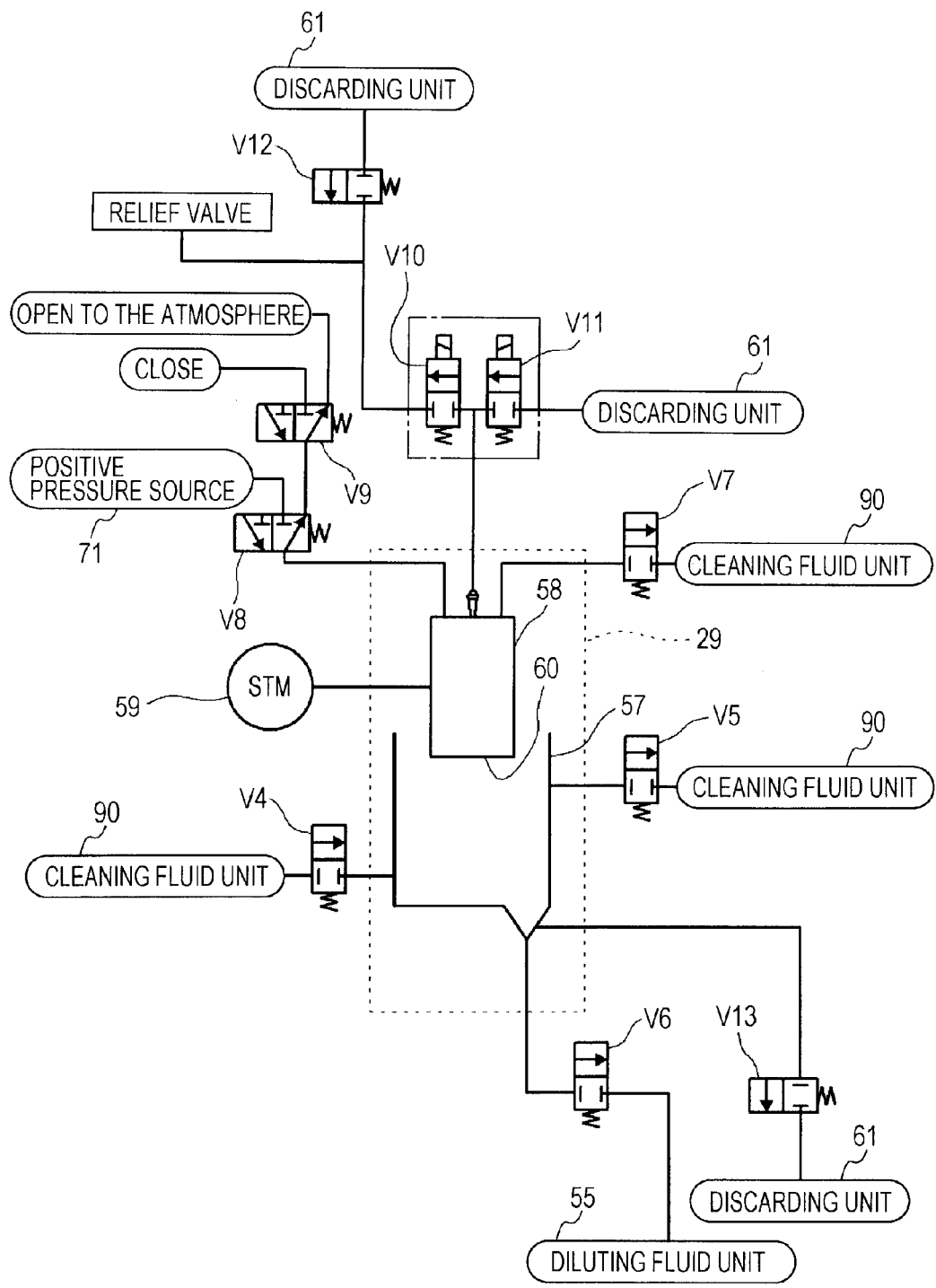
FIG. 12 is a fluid circuit diagram of the preparation device unit.

FIG. 11 is a fluid circuit diagram of the sample setting unit 150 of the preparation device unit 18, the cell dispersing unit 25, the sample pipetting unit 26, the sample quantitating unit 27, the reagent quantitating unit 28, the ultrasonic vibrating unit 100, the liquid removing unit 120, and the reaction unit 24. FIG. 12 is a fluid circuit diagram of the discrimination/substitution unit 29 of the preparation device unit 18.

The sample setting unit 150 includes a rack set region for setting a rack 151 which can mount the biological sample container 53 and has a function to convey the mixed solution of the biological samples and the preservative solution in the biological sample container 53 set in the rack 151 to a position where the mixed solution can be aspirated by a first pipette 26A to be described later.

The cell dispersing unit 25 includes a stirring rod 25A which stirs the mixed solution of the biological samples and the preservative solution in a dispersion container and a driving unit 25B which rotates the stirring rod 25A. The driving unit 25B including a DC motor inserts the stirring rod 25A into the dispersion container and rotates them. Thus, the mixed solution discharged to the dispersion container is stirred by the first pipette 26A to be described later, so that the cells contained in the biological samples can be dispersed.

The sample pipetting unit 26 includes a first pipette 26A and a second pipette 26B. The first pipette 26A aspirates the mixed solution of the biological samples and the preservative solution in the biological sample containers 53 and discharges the mixed solution to the dispersion container of the cell dispersing unit 25. The first pipette 26A aspirates the dispersed mixed solution after the dispersion process, moves to the substitution container 57 of the discrimination/substitution unit 29 (see FIG. 12), and discharges the mixed solution to the substitution container 57. The mixed solution discharged to the substitution container 57 is discriminated and substituted, and a liquid sample in which the concentration of the cells to be measured is increased is prepared from the discriminated and substituted liquid sample containing the cells to be measured. Thereafter, the first pipette 26A aspirates the liquid sample in which the concentration of the cells to be measured is increased from the substitution container 57, moves to the measurement sample container 54 arranged in the container mounting part 130 (see FIG. 4), and discharges the liquid sample to the measurement sample container 54. The second pipette 26B discharges a reagent such as a stain solution which is supplied from the reagent quantitating unit 28 to the measurement sample container 54.

The sample quantitating unit 27 includes a quantitative cylinder 27A and a driving unit 27B including a stepping motor which moves a quantitative piston inserted into the cylinder 27A up and down. The quantitative cylinder 27A is connected to the first pipette 26A through a duct via a direction switching valve V1.

As shown in FIG. 12, the discrimination/substitution unit 29 includes the substitution container 57 having an upwardly opened shape, a piston 58 movable in the substitution container 57 in the up and down direction, and a driving unit 59 including a stepping motor which moves the piston 58 up and down in the substitution container 57.

The substitution container 57 is connected to a cleaning fluid unit 90 through a duct via switching valves V4 and V5. A cleaning fluid is supplied from the cleaning fluid unit 90 to the substitution container 57 via the switching valves V4 and V5. Further, the substitution container 57 is connected to a diluting fluid unit 55 through a duct via a switching valve V6. A diluting fluid is supplied from the diluting fluid unit 55 to the substitution container 57 via the switching valve V6.

The piston 58 includes a hollow cylinder including a filter 60 which does not pass the cells to be measured (epithelial cells) and passes cells having a diameter smaller than that of the cells to be measured (red blood cells, white blood cells, etc.) at the lower part. The piston 58 is connected to a positive pressure source 71 through a duct via a switching valve V8. Thus, a positive pressure can be supplied to the inside of the piston 58 by opening the switching valve V8. The internal space of the piston 58 is connected to the outside via a switching valve V9. The internal space of the piston 58 can be opened to the atmosphere by opening the switching valve V9.

The piston 58 is connected to a discarding unit 61 of filtrate through a duct via switching valves V10 and V12. Thus, a filtrate aspirated from the inside of the piston 58 is discarded to the outside through the switching valves V10 and V12.

The piston 58 is connected to the cleaning fluid unit 90 through a duct via a switching valve V7. The cleaning fluid supplied from the cleaning fluid unit 90 is used for cleaning the piston 58 and the substitution container 57. The cleaning fluid which has cleaned the piston 58 and the inside of the substitution container 57 is discharged to the discarding unit 61 via switching valves V11 and V13.

Returning to FIG. 11, the reagent quantitating unit 28 includes a pair of quantitative cylinders 28A and 28B and a driving unit 28C including a stepping motor which moves quantitative pistons inserted into each of the cylinders 28A and 28B, respectively up and down. Each of the quantitative cylinders 28A and 28B is connected to the second pipette 26B through a duct via supply switching valves V2 and V3, respectively. A reagent quantified by each of the quantitative cylinders 28A and 28B is supplied to the second pipette 26B via the supply switching valves V2 and V3 and discharged to the measurement sample container 54.

Thus, the liquid sample in which the concentration of the cells to be measured is increased, being held in the measurement sample container 54 of the reaction unit 24, can be mixed with a plurality types of reagents quantified by the quantitating unit 28 in a predetermined amount.

In the present embodiment, there are two types of reagents to be quantified by each of the quantitative cylinders 28A and 28B of the reagent quantitating unit 28. The reagent to be added to the biological samples after weighting it by the one quantitative cylinder 28A is a stain solution for performing PI staining. The reagent to be added to the biological samples after weighting it by the other quantitative cylinder 28B is RNase for subjecting cells to a RNA process. The PI staining is performed with propidium iodide (PI) which is a fluorescent staining solution containing a pigment. Since nuclei are selectively stained in the PI staining, the fluorescence from the nuclei can be detected. The RNA process is a process of melting RNA in cells. Since the dye solution stains both RNA and DNA of epithelial cells, RNA is melted by performing the RNA process and is not stained by the dye solution. Therefore, the DNA of a cell nucleus can be accurately measured.

The reaction unit 24 includes a circular rotatable table 24A and a driving unit 24B which rotates and drives the circular rotatable table 24A. The driving unit 24B includes a stepping motor. A holder capable of setting the measurement sample containers 54 which hold the liquid sample prepared by the discrimination/substitution unit 29 in which the concentration of the cells to be measured is increased is provided in the outer periphery part of the rotating table 24A.

The operation control of the driving units and the switching valves (electromagnetic valves) V1 to V13 in each unit shown in FIGS. 11 and 12 is performed based on a control command from the preparation control unit 16 (microprocessor 19).

[Configuration of the Discrimination/Substitution Unit]

Figure 13:
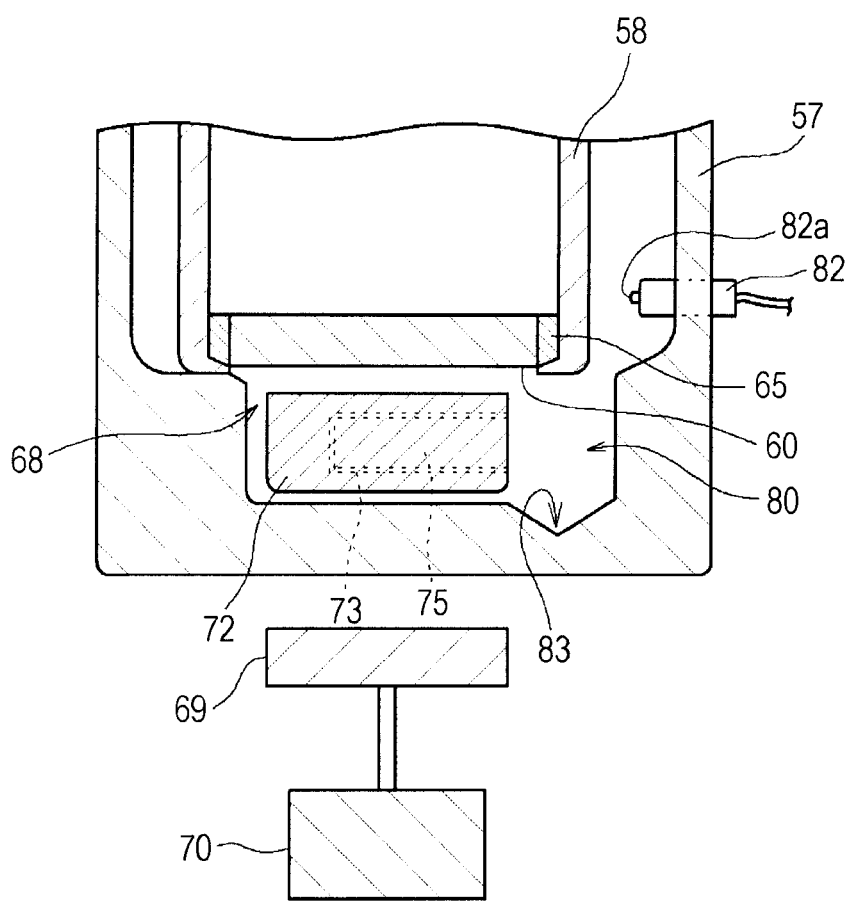
FIG. 13 is a cross sectional explanatory view of a substitution container.
Figure 14A:
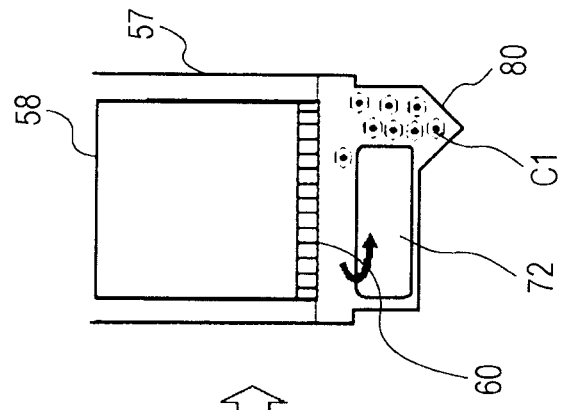
FIG. 14 is a pattern diagram showing a process for concentrating analytes in a discrimination/substitution unit.
Figure 14B:
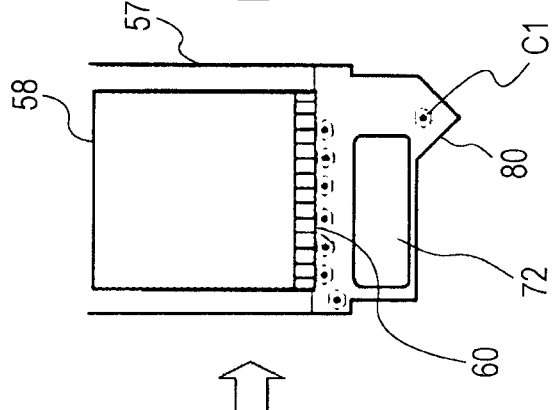
Figure 14C:
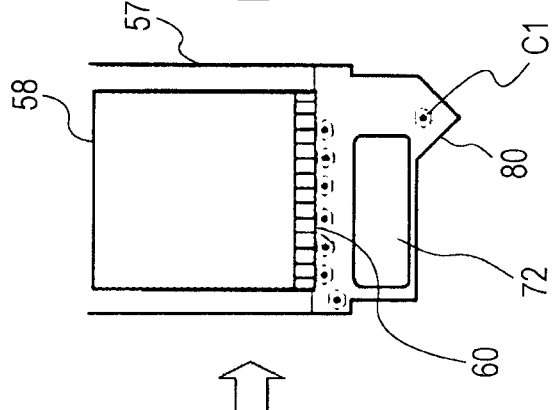
Figure 14D:
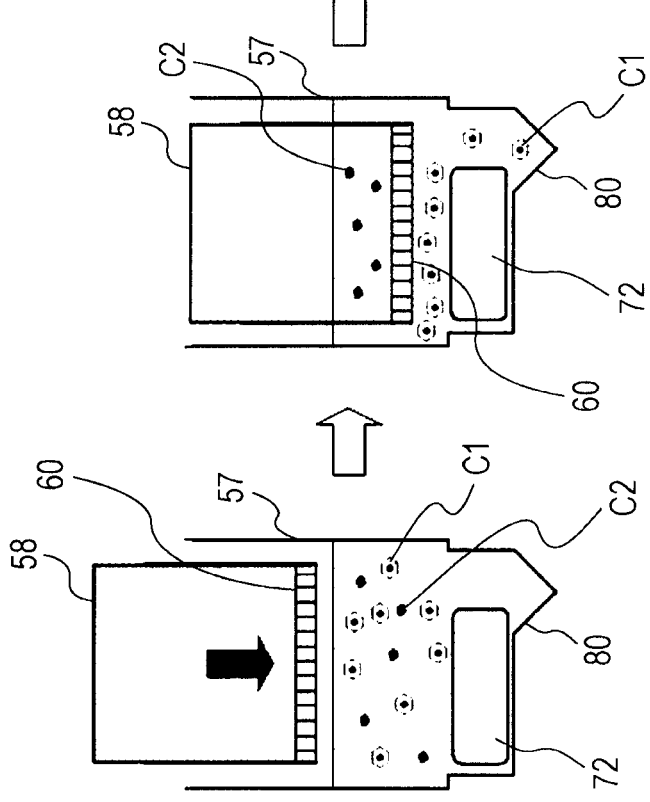

The configuration of the discrimination/substitution unit 29 in the present embodiment will be described with reference to FIG. 13. FIG. 13 is a cross sectional explanatory view of the vicinity of the bottom of the substitution container 57 in the discrimination/substitution unit 29 of FIG. 12 in the present embodiment.

As shown in FIG. 13, the discrimination/substitution unit 29 of the present embodiment includes the substitution container 57, the piston 58 made of a cylindrical body movable in the substitution container 57 in the up and down direction, a filter 60 for sorting the cells to be measured which is arranged at the lower part of the piston 58 made of a cylindrical body, and a liquid surface detection sensor 82 which detects the surface of the liquid containing the cells to be measured.

The substitution container 57 includes a holding chamber 68 which can hold analytes to be analyzed (the cells to be measured) and a condensed sample holding chamber 80 which is communicated with and arranged in the holding chamber. The rotor 72 (rotating member) which moves the cells to be measured contained in the liquid sample from the holding chamber 68 to the condensed sample holding chamber 80 is held in the holding chamber 68. The rotor 72 is configured to be rotated by the magnetic force and includes the magnet 69 for providing the magnetic force to the rotor 72 and the driving motor 70 for rotating the magnet 69 on the lower side of the bottom of the holding chamber 68.

The rotor 72 has a circular cylindrical shape and is made of polychloro-trifluoroethylene (PCTFE), and the like. A hole 73 facing the center is formed in the peripheral surface of the rotor 72. A magnet 75 having a round bar shape is contained in the hole 73.

The filter 60 is arranged on the bottom of the piston 58 through a holding fixture 65. The piston 58 serves as a liquid separating unit which separates a liquid into a first liquid which mainly contains the cells to be measured and a second liquid which mainly contains cells having a diameter smaller than that of the cells to be measured by passing the liquid through the filter 60.

In the present embodiment, epithelial cells of the uterine cervix are assumed as the cells to be measured. The size of the epithelial cells is from about 20 to 80 μm (the average size is about 60 μm). The size of red blood cells which are cells smaller than the cells to be measured is from about 7 to 10 μm. Similarly, the size of white blood cells which are cells smaller than the cells to be measured is from about 8 to 15 μm. The size of contaminants such as bacteria is from about 1 to several μm.

Then, the filter 60 in the present embodiment is made of metal having through holes with a diameter smaller than 20 μm (a diameter of 8 to 20 μm) by Chemical Vapor Deposition (CVD) so that epithelial cells do not pass the through holes of the filter 60 even in a state where pressure is applied to the liquid in the substitution container 57 and do not move to the piston 58. The through holes of the CVD filter made of metal have little deformation as compared with other filters made of resin and even a filter made of metal mesh, which is advantageous for improving an aperture ratio.

The pore diameter of the filter 60 has been set to the range of 8 to 20 μm, because many phenomena that the through holes are clogged with the cells and the contaminants at an early stage are observed when the pore diameter is less than 8 μm, and the epithelial cells pass the through holes more often in a state where pressure is applied to the liquid in the substitution container 57 when the pore diameter exceeds 20 μm. The pore diameter of the filter 60 is more preferably around 15 μm.

The liquid surface detection sensor 82 is arranged at the lower part of the substitution container 57 to detect the surface of the first liquid in the substitution container 57. The liquid surface detection sensor 82 is a capacitance type sensor and the distal end of the liquid surface detection sensor 82 is projected from the inner surface of the substitution container 57 to the inner side by about 2 to 3 mm. A sensor unit 82*a* having a pin shape is provided on the distal end of the projected portion.

The liquid surface detection sensor 82 is used to detect that the surface of the first liquid containing the cells to be measured has reached the position, nearly at the bottom of the filter 60.

In the present embodiment, the sensor unit 82*a* is arranged at the upper side by about 2.0 mm relative to the lower surface of the filter 60 and the aspiration of the second liquid in the piston 58 is stopped after a lapse of predetermined time after the detection signal is received from the sensor unit 82*a* taking into consideration the influence of the surface tension and the aspiration rate of the second liquid. The sensor unit 82*a* having a pin shape is arranged at the obliquely upper side, whereby draining of the liquid can be improved and the accuracy of the liquid surface detection can be improved. In this case, an angle to arrange the sensor with respect to a horizontal surface is in the range of about 5 to 90 degrees.

In the present embodiment, the holding chamber 68 and the condensed sample holding chamber 80 communicated with and arranged in the periphery part of the holding chamber 68 are arranged at the bottom of the substitution container 57. The condensed sample holding chamber 80 plays a role in collecting the cells to be measured which have been moved by the rotation of the rotor 72 held in the holding chamber 68. Some of the cells to be measured are attached on the lower surface of the filter 60 by the discrimination operation to be described later. The attached cells to be measured are torn from the lower surface of the filter 60 by the rotation of the rotor 72 and collected into the condensed sample holding chamber 80 communicated with and arranged in the periphery part of the holding chamber 68 by a centrifugal force generated by the rotation of the rotor 72.

Here, a process of the present embodiment in which the mixed solution of the biological samples and the preservative solution is discriminated and the liquid sample in which the concentration of the cells to be measured is increased is prepared from the liquid sample containing the cells to be measured which has been discriminated will be described in detail with reference to the pattern diagram of FIG. 14.

As shown in FIG. 14(*a*), the piston 58 is lowered so that the filter 60 moves downward from the upper side of the surface of the mixed solution of the biological samples and the preservative solution in the substitution container 57 to the solution.

Then, as shown in FIG. 14(*b*), the liquid containing the cells to be measured (C1) (the first liquid) remains at the lower side of the filter 60 in the substitution container 57 and the liquid containing cells having a diameter smaller than that of the cells to be measured (C2) (the second liquid) remains at the upper side of the filter 60 (inside of the piston 58).

Thereafter, as shown in FIG. 14(*c*), the second liquid remaining in the piston 58 is discharged to the outside. In this case, the second liquid is aspirated by applying a negative pressure to the inside of the piston 58, and thus some of the cells to be measured (C1) contained in the first liquid are attached to the lower side of the filter 60.

As shown in FIG. 14(*d*), the cells to be measured attached to the lower side of the filter 60 are torn by rotating the rotor 72 and the cells to be measured contained in the first liquid are held in the condensed sample holding chamber. The measurement sample with a high concentration of the cells to be measured can be obtained by obtaining the liquid containing the cells to be measured held in the condensed sample holding chamber.

As shown in FIG. 13, a taper 83 whose cross section gradually decreases toward the lower side is formed at the bottom of the condensed sample holding chamber 80. The liquid sample held in the condensed sample holding chamber 80 is aspirated by the first pipette 26A which is a liquid obtaining unit. At that time, the distal end of the first pipette 26A is configured to lower to near the distal end of the taper 83 and to aspirate the liquid sample from near the distal end. Thus, the liquid sample can be used without waste by aspirating the liquid sample in the condensed sample holding chamber 80 as much as possible.

[Processing Operation]

Next, the processing operation of the cell analyzer 1 mentioned above will be described.

Figure 15:
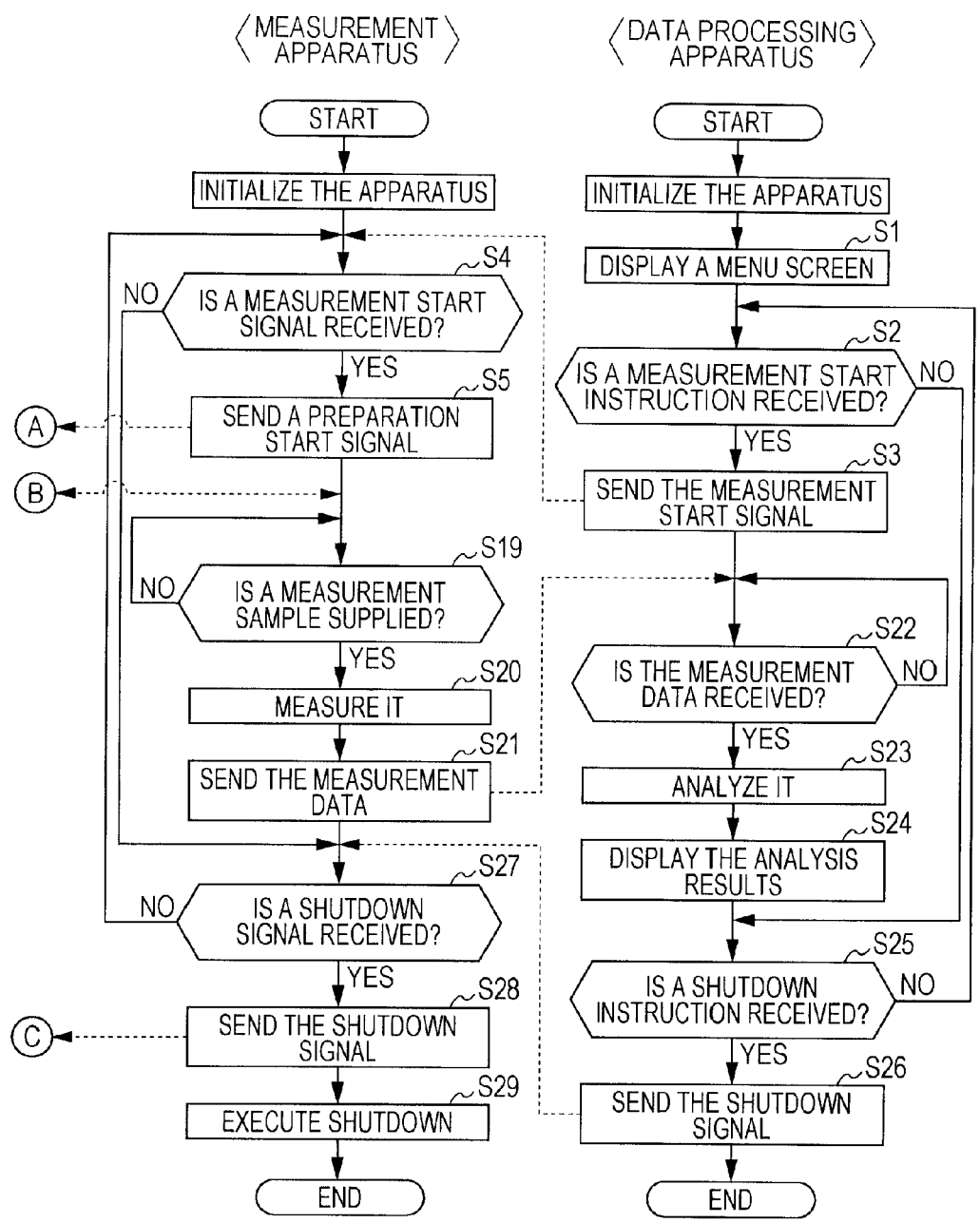
FIG. 15 is a flow chart showing processes which are performed by each control unit of the cell analyzer.
Figure 16:
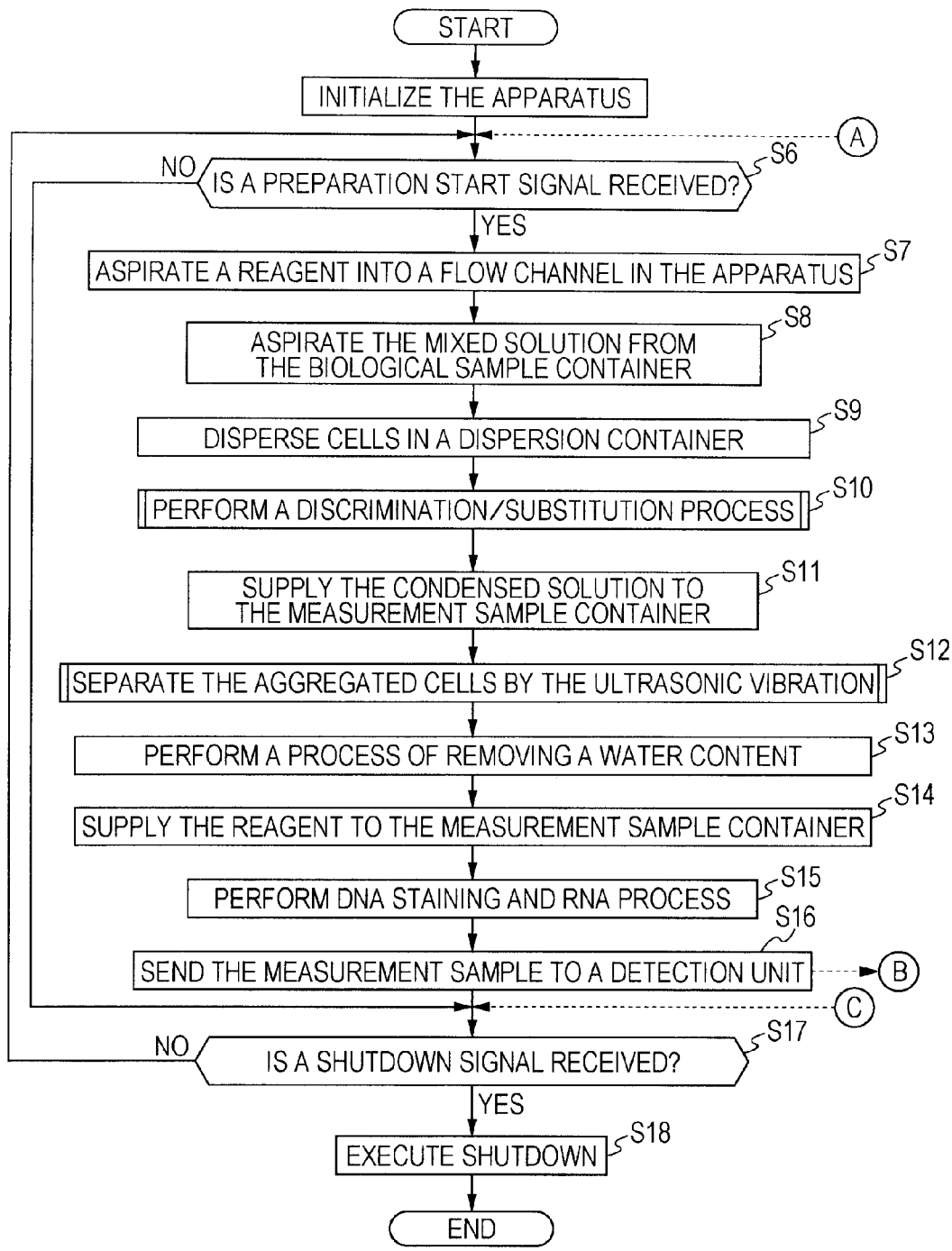
FIG. 16 is a flow chart showing processes which are performed by each control unit of the cell analyzer.

FIGS. 15 and 16 are flow charts showing processes performed by each of the control units 8, 16, and 31 in the cell analyzer 1.

In FIG. 15, a process flow performed by the control unit (processing body) 31 of the data processing apparatus 4 is shown in the right column and a process flow performed by the control unit 8 of the measurement apparatus 2 is shown in the left column. In FIG. 16, a process flow performed by the control unit 16 of the sample preparation apparatus 3 is shown in a line. The process flow is connected to the process flow of FIG. 15 at points A, B, and C. Hereafter, the processing content performed by the cell analyzer 1 will be described with reference to FIGS. 15 and 16.

First, a control unit 31 of the data processing apparatus 4 displays a menu screen on the display 32 (step S1). Thereafter, when a measurement start instruction according to the menu screen is received from the input unit 33 (step S2), the control unit 31 of the data processing apparatus 4 sends a measurement start signal to the measurement apparatus 2 (step S3).

When receiving the measurement start signal (step S4), the control unit 8 of the measurement apparatus 2 sends a preparation start signal to the sample preparation apparatus 3 (step S5 and point A).

The preparation control unit 16 of the sample preparation apparatus 3 supplies the liquid 103 from the liquid supply source 106A to the concave portion 104 of the liquid holding part 101 in the initialization process. When receiving the preparation start signal (step S6) as shown in FIG. 16, the preparation control unit 16 aspirates the reagent to be used for preparation of the measurement sample (stain solution, RNase) into a flow channel in the apparatus, and sends the mixed solution of the biological samples and the preservative solution containing methanol as a main ingredient held in the biological sample container 53 to the dispersion container of the cell dispersing unit 25. Then, the preparation control unit 16 makes the cell dispersing unit 25 disperse the cells in the mixed solution (steps S7 to S9).

Thereafter, the preparation control unit 16 of the sample preparation apparatus 3 allows only a predetermined amount of the mixed solution after dispersion to be aspirated from the dispersion container, sends the mixed solution to the substitution container 57 of the discrimination/substitution unit 29, and makes the discrimination/substitution unit 29 perform the discrimination/substitution process of the mixed solution of the biological samples and the preservative solution (step S10).

[Content of the Discrimination/Substitution Process]

Figure 17:
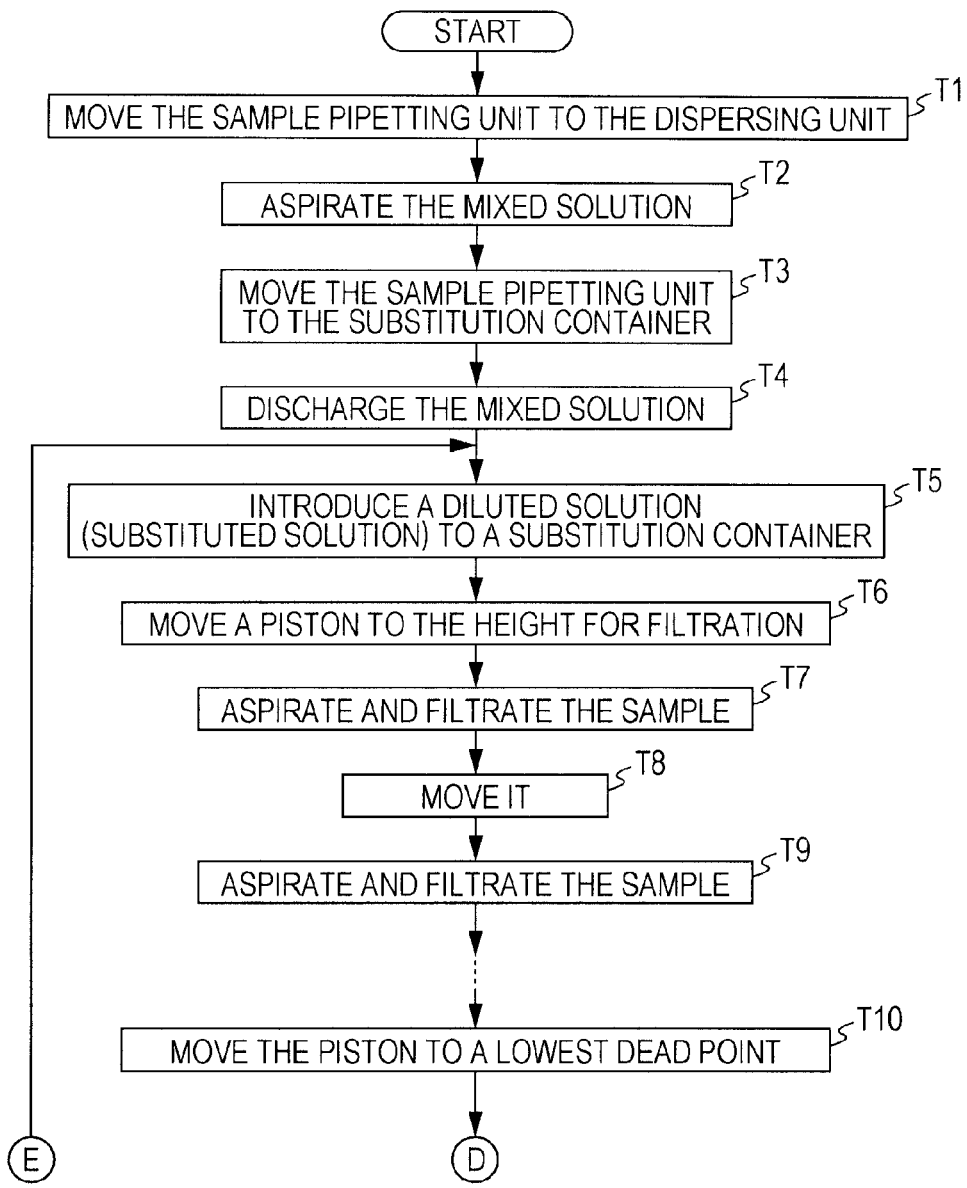
FIG. 17 is a flow chart showing a discrimination/substitution process.
Figure 18:
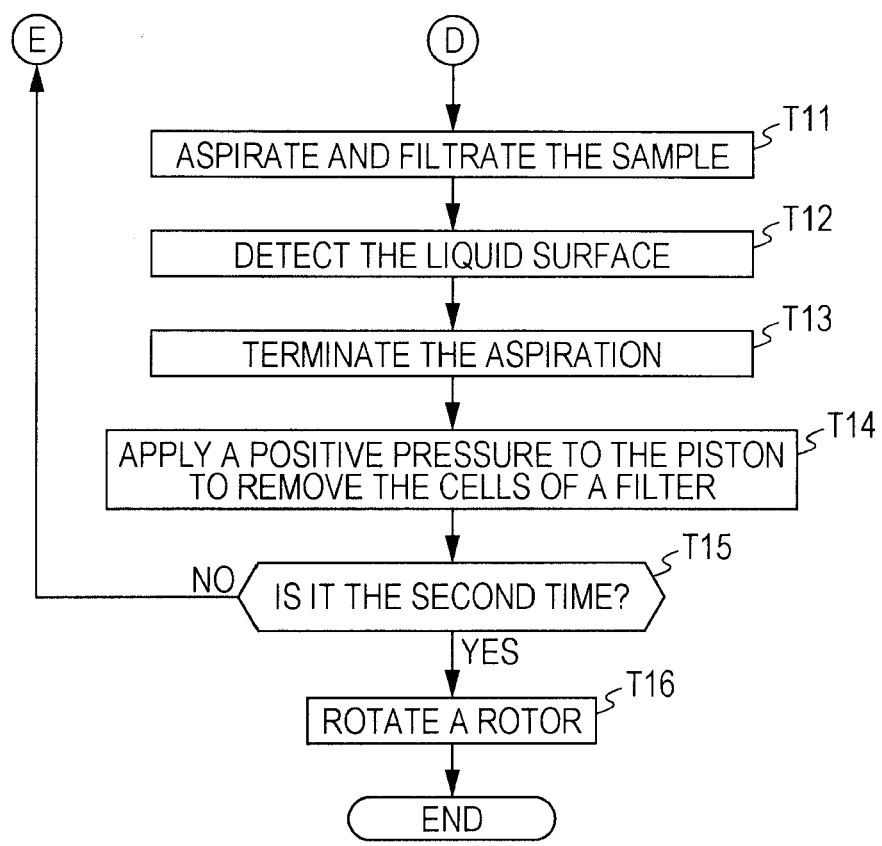
FIG. 18 is a flow chart showing a discrimination/substitution process.

FIGS. 17 and 18 are flow charts showing the discrimination/substitution process (step S10).

As shown in FIG. 17, the preparation control unit 16 of the sample preparation apparatus 3 first moves the sample pipetting unit 26 to the cell dispersing unit 25 (step T1) and allows the mixed solution after dispersion to the sample pipetting unit 26 to be aspirated from the dispersion container for a predetermined amount (step T2).

Then, the preparation control unit 16 moves the sample pipetting unit 26 to the substitution container 57 (step T3) and makes the first pipette 26 discharge the mixed solution aspirated to the substitution container 57 (step T4).

Then, the diluted solution (substituted solution) is introduced from the diluting fluid unit 55 to the substitution container 57 via the valve V6 (step T5).

Then, the piston 58 is moved downward up to a predetermined height for filtration by the driving unit 59 (step T6) and the mixed solution in the substitution container 57 is aspirated into the piston 58 and filtrated (step T7). At the time of aspiration and filtration, the valves V10 and V12 to which a relief valve is connected are used. In this case, the relief valve is set to −5 kpa. Thus, at the time of aspiration and filtration, a pressure of about −3 kpa is applied to the filter 60 arranged at the bottom end of the piston 58. The liquid is aspirated and filtrated with such a weak negative pressure, and thus filtration can be performed without allowing the cells to be measured to pass the filter 60 and to be discharged to the discarding unit 61.

Then, the piston 58 is moved to the lower side by the driving unit 59 (step T8) and the mixed solution in the substitution container 57 is aspirated into the piston 58 and filtrated, similar to step T7 (step T9).

When the movement of the piston 58 and the aspiration and filtration of the mixed solution are repeated at a predetermined number of times and the piston 58 moves to a predetermined lowest dead point (step T10), the sample in the substitution container 57 is aspirated into the piston 58 and filtrated, similar to step T7 (step T11). When the sensor unit 82a of the liquid surface detection sensor 82, which is the capacitance type sensor, arranged in the substitution container 57 detects the liquid surface (step T12), the aspiration is stopped after a lapse of predetermined time (step T13). In this case, the liquid sample containing the cells to be measured is filled in the holding chamber 68 arranged at the bottom of the substitution container 57 and the condensed sample holding chamber 80.

Then, the positive pressure is applied to the piston 58 to remove cells (substances to be analyzed) blocked in the through holes of the filter 60 or attached to the lower surface of the filter 60 and to return to the substitution container 57 (the holding chamber 68 and the condensed sample holding chamber 80) (step T14).

Here, the preparation control unit 16 of the sample preparation apparatus 3 determines whether or not the movement to the lowest dead point of the piston 58 is the second time (step T15).

The preparation control unit 16 of the sample preparation apparatus 3 repeats the filtration after introduction of the diluted solution to a substitution spitz when the movement to the lowest dead point of the piston 58 is not the second time (step T5), and proceeds to step T16 when it is the second time.

In step T16, the rotor 72 is rotated by making the driving motor 70a rotate the magnet 69 to remove the cells to be measured attached to the lower surface of the filter 60, and the cells to be measured contained in the liquid sample in the holding chamber 68 are moved to the direction of the condensed sample holding chamber 80 to allow the cells to be measured to be held in the condensed sample holding chamber 80 (step 16).

The liquid (condensed solution) mainly containing the cells to be measured (epithelial cells) in which the number of cells other than the cells to be measured is reduced can be obtained by the discrimination/substitution process. In the discrimination/substitution process, the concentration of methanol in the preservative solution in the liquid supplied from the biological sample container 53 to the substitution container 57 (the mixed solution of the biological samples and the preservative solution) can be diluted by substituting most of the preservative solution with the diluted solution. Thus, in a DNA staining process to be described later, the influence of the preservative solution can be reduced and DNA of the cells to be measured can be well stained.

In the discrimination/substitution process, since the substitution process of the preservative solution and the diluted solution can be performed while performing the discrimination process of cells, the discrimination process and the substitution process can be performed in a shorter time than when these two processes are performed separately.

In the discrimination/substitution process, the cells to be measured (epithelial cells) attached to the lower surface of the filter 60 are detached by the shearing force by rotating the rotor 72 to allow the detached cells to be suspended in the first liquid of the lower side of the filter 60, and the cells to be measured (epithelial cells) blocked in the through holes of the filter 60 are removed by applying pressure from the upper side of the filter 60 to the through holes of the filter 60 to allow the cells to be suspended in the first liquid of the lower part of the filter 60. Thus, the cells to be measured (epithelial cells) attached to the filter can be efficiently recovered without loss of them.

In the present embodiment, the condensed sample holding chamber 80 is communicated with and arranged at the periphery part of the holding chamber 68, and thus the cells to be measured contained in the liquid sample in the holding chamber 68 are collected into the condensed sample holding chamber 80 by rotation of the stirrer 72. Thus, the concentration of the cells to be measured contained in the liquid sample in the holding chamber 68 becomes lower, while the concentration of the cells to be measured contained in the liquid sample in the condensed sample holding chamber 80 becomes higher. Therefore, the measurement sample in which the concentration of the cells to be measured is increased can be obtained by obtaining the liquid sample from the condensed sample holding chamber 80. Some of the cells to be measured are condensed in the collection process, which causes mutual aggregation of the cells, but the aggregated cells to be measured are separated by ultrasonic vibration applying operation to be described later.

[Preparation of the Measurement Sample]

Returning to FIG. 16, the preparation control unit 16 of the sample preparation apparatus 3 moves the sample pipetting unit 26 to the substitution container 57, aspirates a condensed solution from the condensed sample holding chamber 80 into the first pipette 26A, moves the sample pipetting unit 26 to the container mounting part 130, and supplies the condensed solution to the measurement sample container 54 transported from the reaction unit 24 to the container mounting part 130 by the container transporting unit 110 in advance (step S11).

Then, the preparation control unit 16 of the sample preparation apparatus 3 makes the ultrasonic vibrating unit 100 perform the separation process of the aggregated cells (step S12).

[Content of the Separation Process of the Aggregated Cells]

Figure 19:
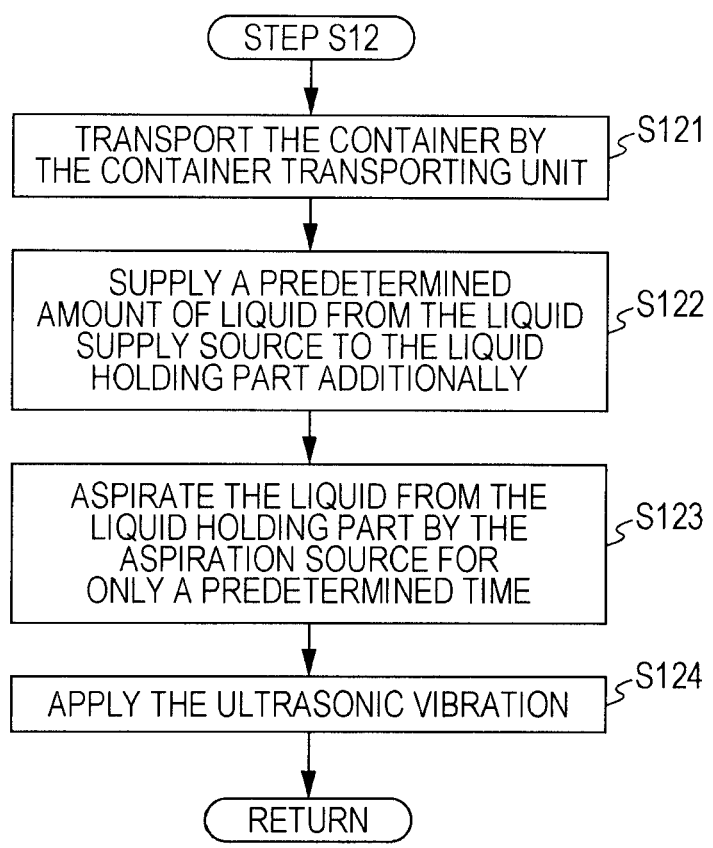
FIG. 19 is a flow chart showing a separation process of aggregated cells by ultrasonic vibration.
Figure 20:
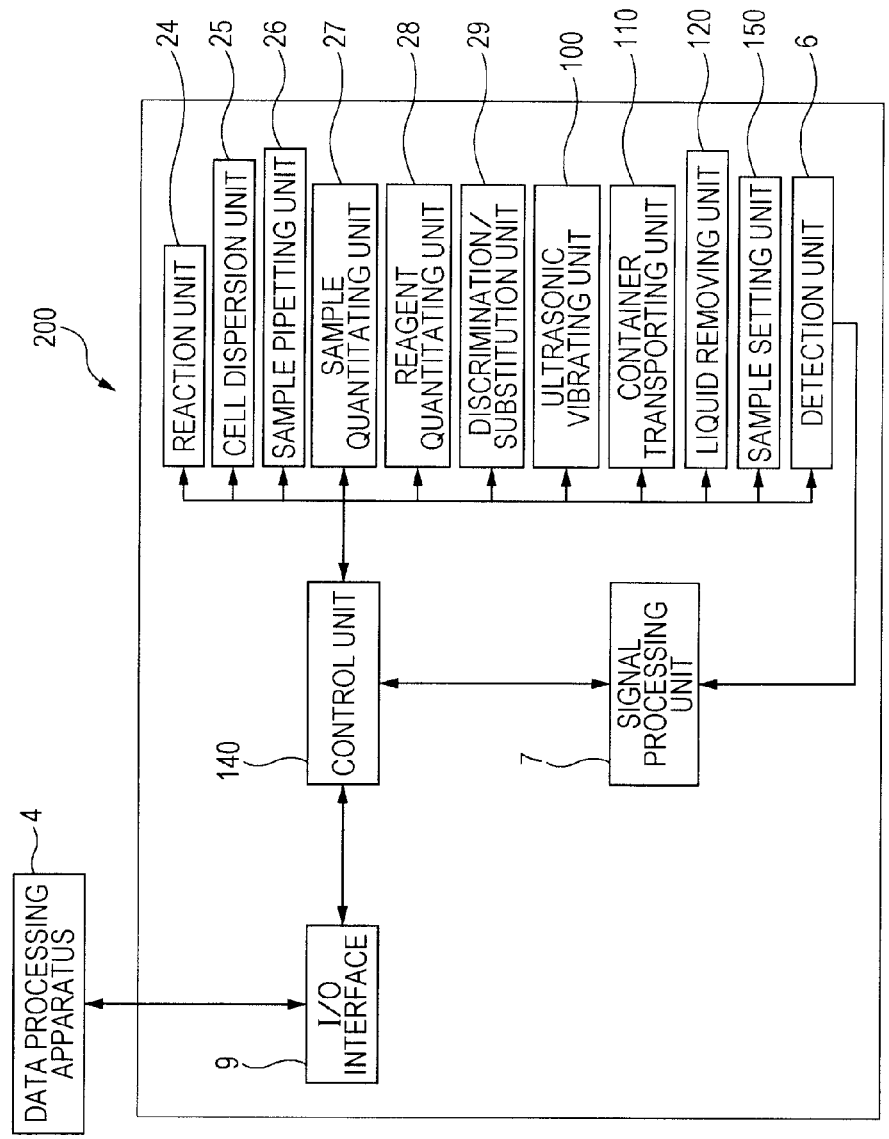
FIG. 20 is a block diagram of an internal configuration of the measurement apparatus according to another embodiment of the present invention.

FIG. 19 is a flow chart showing the separation process of the aggregated cells (step S12).

As shown in FIG. 19, the preparation control unit 16 of the sample preparation apparatus 3 first allows the container transporting unit 110 to move the measurement sample container 54 from the container mounting part 130 to a predetermined position in the ultrasonic vibrating unit 100 (the position shown in FIG. 5) and immerses a part of the container (the lower part) in the liquid (aqueous solution) in the liquid holding part 101 (step S121).

Then, the preparation control unit 16 of the sample preparation apparatus 3 allows the liquid supply source 106A to communicate with the concave portion 104 of the liquid holding part 101 by switching the flow channel switching valve 162 and additionally supplies a predetermined amount of the liquid 103 (an amount that the liquid surface exceeds d of FIG. 5) from the liquid supply source 106A to the concave portion 104 of the liquid holding part 101 (step S122).

Then, the preparation control unit 16 of the sample preparation apparatus 3 aspirates the liquid 103 from the concave portion 104 of the liquid holding part 101 for only a predetermined time by driving the aspiration source 107A and controls so as to have the depth d of the liquid 103 (depth of the liquid with the measurement sample container 54 immersed) (step S123). Thereby, the ultrasonic vibration can be effectively generated.

Then, the ultrasonic vibration is applied to the condensed solution in the measurement sample container 54 being held with the container immersed in the liquid by the container transporting unit 110 by the ultrasonic transducer 102 and the cells to be measured being aggregated in the condensed solution are separated (step S124).

In the present embodiment, the ultrasonic vibrating unit 100 is controlled to apply the ultrasonic vibration to the epithelial cells which are substances to be analyzed with predetermined output and time without causing damages that affect the analysis in the ultrasonic process.

In order to improve dispersion effects of the aggregated cells, the output of the ultrasonic vibration may be increased and/or the time for applying the ultrasonic vibration may be lengthened. When the ultrasonic vibration is applied to the condensed solution in the measurement sample container 54, the aggregated cells contained in the condensed solution are dispersed. On the other hand, the temperature of the condensed solution is increased due to vibration of the liquid.

Table 1 shows results of elevated values of the solution temperature in the measurement sample container 54 as for the measurement sample container (cuvette) 54 made of polypropylene and the measurement sample container 54 made of polyethylene examined when the output of the ultrasonic vibration was set to 14 W, 16 W, and 18 W, respectively. The time for applying the ultrasonic vibration was set to 5 seconds or 10 seconds. About 530 µl of water was held in the measurement sample container 54 as the measurement sample and the solution temperature was measured with a thermocouple. The room temperature at the time of measurement was from 24.1 to 25.0 degrees. The experiment was performed three times under respective conditions and the average value was calculated.

TABLE 1

| Increase in the solution temperature in the cuvette | | (Material: polypropylene) Time | | (Material: Polyethylene) Time | |
|---|---|---|---|---|---|
| | | 5 Seconds | 10 Seconds | 5 Seconds | 10 Seconds |
| Output | 14 W | 2.7 | 5.4 | 2.2 | 3.3 |
| | 16 W | 3.0 | 5.2 | 2.6 | 4.2 |
| | 18 W | 3.1 | 5.7 | 2.9 | 4.6 |

From Table 1, it is found that as the output of the ultrasonic vibration becomes higher or as the time for applying the ultrasonic waves becomes longer, an increase in the solution temperature in the measurement sample container 54 becomes larger. It is found that there are differences in the increased temperature of the solution temperature in the measurement sample container 54 due to a difference between the materials of the measurement sample container 54 and the increase in temperature in the case of polypropylene is larger than that in the case of polyethylene. For example, when comparing under conditions that the output of the ultrasonic vibration is 18 W and the time for applying the ultrasonic vibration is 10 seconds, the solution temperature in the measurement sample container 54 in the case of polypropylene became higher by about 1 degree than that in the case of polyethylene. This is because in the case of polypropylene, the ultrasonic waves are easily transmitted to the liquid in the measurement sample container 54 as compared to the case of polyethylene, resulting in an increase of the solution temperature in the measurement sample container 54. Therefore, polypropylene is preferable to polyethylene as the material of the inside of the measurement sample container 54 from the viewpoint of dispersing the aggregated cells effectively. It is found that when the material of the measurement sample container 54 is polypropylene, the solution temperature in the cuvette can be controlled so as to be about 31 degrees (an increase in temperature is from about 5 to 6 degrees) at an ultrasonic output of 14 to 16 W if the time for applying the ultrasonic waves is less than 10 seconds.

Returning to FIG. 16, the preparation control unit 16 of the sample preparation apparatus 3 allows the container transporting unit 110 to move the measurement sample container 54 from the ultrasonic vibrating unit 100 to the liquid removing unit 120 and removes a water content attached to the outer periphery surface of the measurement sample container 54 by spraying air and aspirating and discharging it in the liquid removing unit 120 (step S13).

Then, the preparation control unit 16 of the sample preparation apparatus 3 makes the container transporting unit 110 move the measurement sample container 54 from the liquid removing unit 120 to the reaction unit 24. The preparation control unit 16 of the sample preparation apparatus 3 sends the stain solution and RNase stored in the apparatus from the reagent quantitating unit 28 to the second pipette 26B, the second pipette 26B supplies the stain solution and RNase which have been sent to the measurement sample container 54 (step S14) and produces the measurement sample by performing DNA staining and RNA process in the measurement sample container 54 (step S15).

After the completion of the process, the obtained measurement sample is quantified by the sample quantitating unit 27 through the first pipette 26A and supplied to the detection unit 6 of the measurement apparatus 2 after quantification (step S16 and point B).

The preparation control unit 16 of the sample preparation apparatus 3 always determines whether or not the shutdown signal from the measurement apparatus 2 is received (step S17 and point C), returns to step S6 for determining whether or not the preparation start signal is received when the signal is not received, and executes the shutdown to terminate the process of preparing the sample when the signal is received (step S18). In the shutdown process, the preparation control unit 16 of the sample preparation apparatus 3 allows the concave portion 104 of the liquid holding part 101 to communicate with the chamber 108 by switching the flow channel switching valve 162, and then makes the whole liquid 103 discharged from the concave portion 104 by driving the aspiration source 107A.

[Measurement by the Measurement Apparatus and its Data Analysis]

Returning to FIG. 15, after sending the preparation start signal, the control unit 8 of the measurement apparatus 2 always determines whether or not the measurement sample is supplied from the sample preparation apparatus 3 (step S19).

When the measurement sample is sent from the sample preparation apparatus 3 (point B), the control unit 8 of the measurement apparatus 2 sends the measurement sample to the flow cell 45 of a measurement unit 14, performs the measurement of cells of the measurement sample (step S20), and sends the measurement data to the data processing apparatus 4 (step S21).

On the other hand, after sending the measurement start signal, the control unit 31 of the data processing apparatus 4 always determines whether or not the measurement data is received from the measurement apparatus 2 (step S22).

When receiving the measurement data from the measurement apparatus 2, the control unit 31 of the data processing apparatus 4 analyzes the cells and nuclei using the measurement data and determines whether or not the cells in the measurement sample become cancerous (step S23).

The control unit 31 of the data processing apparatus 4 displays the analysis results on the display 32 (step S24) and determines whether or not a shutdown instruction is input by the user (step S25).

When the shutdown instruction is input, the control unit 31 of the data processing apparatus 4 sends a shutdown signal to the measurement apparatus 2 (step S26).

The measurement control unit 8 of the measurement apparatus 2 always determines whether or not the shutdown signal from the data processing apparatus 4 is received (step S27), returns to step S4 for determining whether or not the measurement start signal is received when the signal is not received, transfers the shutdown signal to the sample preparation apparatus 3 when the signal is received (step S28), and executes the shutdown to terminate the measurement process (step S29).

In the present invention, the aggregated cells to be measured in the measurement sample are separated by applying ultrasonic vibration to the measurement sample condensed by the discrimination/substitution unit 29 in the ultrasonic vibrating unit 100. Thus, the measurement accuracy can be improved.

Table 3 shows an equation of the rate of aggregated epithelial cells (the rate of aggregated epithelial cells=the number of aggregated epithelial cells/(the number of single epithelial cells+the number of aggregated epithelial cells)) when the ultrasonic process by the ultrasonic vibrating unit was not performed (control), when the ultrasonic process was performed using polypropylene for the measurement sample container (Example 1), and when the ultrasonic process was performed using stainless steel for the measurement sample container (Comparative example 1). Here, water is used as the liquid held in the liquid holding part.

From Example 1, it is found that when polypropylene is used for the measurement sample container, the degree of aggregation of the aggregated epithelial cells is decreased by one sixth compared to the control. From Comparative example 1, it is found that when stainless steel is used for the measurement sample container, the degree of aggregation of the cells to be measured is almost the same as that of the control even if the ultrasonic process is performed.

TABLE 3

|  | Material of cuvette | The number of single epithelial cells | The number of aggregated epithelial cells | The rate of aggregated epithelial cells = the number of aggregated epithelial cells/(the number of single epithelial cells + the number of aggregated epithelial cells |
|---|---|---|---|---|
| Control (without ultrasonic dispersion) | — | 6812 | 834 | 11% |
| Example 1 (with ultrasonic dispersion) | Polyethylene | 5081 | 97 | 2% |
| Comparative example 1 (with ultrasonic dispersion) | Stainless steel | 4913 | 529 | 10% |

As mentioned above, other synthetic resins such as polyethylene except for polypropylene can be used as the material of the measurement sample container. Table 4 shows an equation of the rate of aggregated epithelial cells (the rate of aggregated epithelial cells=the number of aggregated epithelial cells/(the number of single epithelial cells+the number of aggregated epithelial cells)) when polypropylene was used as the material of the measurement sample container and the ultrasonic process by the ultrasonic vibrating unit was not performed, when the ultrasonic process was performed using polypropylene as the material of the measurement sample container (the output of ultrasonic vibration: 15 W, the time for applying ultrasonic vibration: 5 seconds), and when the ultrasonic process was performed using polyethylene as the material of the measurement sample container (the output of ultrasonic vibration: 15 W, the time for applying ultrasonic vibration: 5 seconds). Here, water is used as the liquid held in the liquid holding part.

TABLE 4

|  | The number of single epithelial cells | The number of aggregated epithelial cells | The rate of aggregated epithelial cells = the number of aggregated epithelial cells/(the number of single epithelial cells + the number of aggregated epithelial cells |
|---|---|---|---|
| Control (without ultrasonic dispersion) | 34.316 | 1862 | 5.1% |
| Example 1 (with ultrasonic dispersion) | 32.654 | 646 | 1.9% |
| Comparative example 1 (with ultrasonic dispersion) | 42.860 | 1486 | 3.3% |

From Table 4, it is found that the degree of aggregation of the cells to be measured can be reduced by performing the ultrasonic process when polyethylene is used as the material of the measurement sample container, similar to when polypropylene is used as the material of the measurement sample container. It is estimated that when the conditions of the ultrasonic vibration are the same, an effect of dispersing the cell in the case of polypropylene is higher than that in the case of polyethylene.

[Other Variants]

The disclosed embodiments are illustrative and not restrictive. The scope of the present invention is defined by the attached claims rather than by the embodiments, and all changes equivalent to the configurations of claims are enclosed therein.

For example, in the embodiments, the automation of the ultrasonic process is achieved by transporting the measurement sample container holding the measurement sample to the ultrasonic vibrating unit by the container transporting unit and similarly transporting the measurement sample container after the separation process of the aggregated cells by the ultrasonic vibration by the container transporting unit to the liquid removing unit. However, the measurement sample can be transported to the container arranged in the ultrasonic vibrating unit using a sample transporting means (sample transporting unit) such as a pipette, and the measurement sample after the separation process of the aggregated cells by the ultrasonic vibration can be transported to another container arranged in the sample setting unit similarly using the sample transporting means such as the pipette. In this case, the loss of the measurement sample is increased compared to the embodiments. However, the container transporting unit and the liquid removing unit can be omitted, so that the configuration of the apparatus can be simplified.

In the embodiments, the measurement sample container holding the measurement sample is transported from the container mounting part to the ultrasonic vibrating unit by the container transporting unit, but the present invention is not limited thereto, and the measurement sample may be transported to the measurement sample container arranged in the ultrasonic vibrating unit by, for example, the sample transporting means such as the pipette, or the measurement sample container holding the measurement sample may be transported to the ultrasonic vibrating unit by the user.

In the embodiments, the epithelial cells of the uterine cervix are used as the cells to be measured, but the malignant transformation of buccal cells, epithelial cells of the bladder and the pharynx, and epithelial cells of organs can be determined.

In the embodiments, the measurement sample prepared by the sample preparation apparatus 3 is measured by the flow cytometer, but a smeared specimen preparing apparatus which smears the measurement sample prepared by the sample preparation apparatus 3 on a slide glass to prepare a smeared specimen and a cell image processing apparatus which images the smeared specimen and analyzes epithelial cells in the imaged image may be provided. Since the measurement sample in which the concentration of the epithelial cells which are the cells to be measured is increased and the number of cells, such as red blood cells and white blood cells, is reduced is smeared on the slide glass, the epithelial cells can be analyzed with sufficient accuracy.

In the embodiments, the measurement apparatus and the sample preparation apparatus are separate bodies, but the measurement apparatus and the sample preparation apparatus can also be integrated. FIG. 19 is a block diagram showing an internal configuration of the measurement apparatus 200 when the measurement apparatus and the sample preparation apparatus are integrated. The same numerals are attached to similar configurations to the embodiments, so the description of the configurations is omitted.

As shown in FIG. 19, the measurement apparatus 200 includes the reaction unit 24, the cell dispersing unit 25, the sample pipetting unit 26, the sample quantitating unit 27, the reagent quantitating unit 28, the discrimination/substitution unit 29, an ultrasonic dispersing unit 100, the container transporting unit 110, the liquid removing unit 120, the sample setting unit 150, the detection unit 6, the signal processing unit 7, the control unit 140, and the I/O interface 160.

The control unit 150 of the measurement apparatus 200 has both functions of the measurement control unit 8 of FIG. 2 and the preparation control unit 16 of FIG. 3 according to the embodiments. The control unit 150 is connected to the data processing apparatus 4 via the I/O interface 160 and can transmit and receive data processed by the control unit 150 or data required for the process of the control unit 150 with the data processing apparatus 4.

What is claimed is:

1. A sample preparation apparatus comprising:
   an ultrasonic vibrating unit which applies ultrasonic vibration to a sample including aggregated cells held in a sample container;
   a sample preparation unit which prepares a measurement sample by mixing the sample including the aggregated cells to which the ultrasonic vibration is applied and a predetermined reagent;

a container transporting unit which transports the sample container holding the sample including the aggregated cells from the ultrasonic vibrating unit to the sample preparation unit;
a controller configured to control the container transporting unit to:
  raise the sample container at the ultrasonic vibrating unit to a first position above the ultrasonic vibrating unit;
  move the sample container from the first position to a second position above the sample preparation unit;
  lower the sample container from the second position so as to set the sample container in the sample preparation unit; and
a container mounting part which mounts the sample container, wherein
the container transporting unit transports the sample container from the container mounting part to the ultrasonic vibrating unit, and
the ultrasonic vibrating unit, the sample preparation unit, and the container mounting part are arranged on the same circumference.

2. The apparatus of claim 1, wherein
the ultrasonic vibrating unit includes a liquid holding part which holds a liquid and an ultrasonic transducer which generates ultrasonic vibration;
the container transporting unit is able to hold the sample container, with the sample container immersed in the liquid held in the liquid holding part; and
the ultrasonic transducer applies ultrasonic vibration to the sample including the aggregated cells held in the sample container through the liquid.

3. The apparatus of claim 2, further comprising
a liquid surface controlling unit which controls the height of the surface of the liquid held in the liquid holding part.

4. The apparatus of claim 3, wherein
the liquid surface controlling unit includes a liquid supplying unit which supplies the liquid to the liquid holding part and a liquid discharging unit which discharges the liquid from the liquid holding part.

5. The apparatus of claim 4, wherein
the liquid discharging unit is a discharge hole formed on the peripheral wall of the liquid holding part.

6. The apparatus of claim 2, wherein
the container transporting unit is able to hold the sample container with the sample container immersed in the liquid held in the liquid holding part so that the surface of the sample in the sample container is positioned at the lower side than the surface of the liquid in the liquid holding part.

7. The apparatus of claim 2, wherein
the sample container is made with a material having an acoustic impedance equivalent to an acoustic impedance of the liquid held in the liquid holding part.

8. The apparatus of claim 7, wherein
the liquid is water and the sample container is made with a synthetic resin.

9. The apparatus of claim 8, wherein the sample container is made with polypropylene.

10. The apparatus of claim 1, wherein
the arithmetic average roughness of the inner surface of the sample container is in a range of 1 to 30 μm.

11. The apparatus of claim 2, wherein
the liquid holding part has a cylindrical body shape, the ultrasonic transducer has a circular cylindrical shape, and an inner diameter of the liquid holding part is larger than that of the ultrasonic transducer.

12. The apparatus of claim 1, wherein
the ultrasonic vibrating unit applies ultrasonic vibration to the aggregated cells to be analyzed with predetermined output and time without causing damages that affect the analysis.

13. The apparatus of claim 2, wherein the frequency of the ultrasonic transducer is in a range of 20 to 75 kHz.

14. The apparatus of claim 1, further comprising
a container mounting part which mounts the sample container,
wherein the container transporting unit transports the sample container from the container mounting part to the ultrasonic vibrating unit.

15. The apparatus of claim 1, further comprising
a sample dispensing unit which dispenses the sample to the sample container.

16. The apparatus of claim 15, wherein the sample dispensing unit dispenses the sample to the sample container mounted in the container mounting part; and
the container transporting unit which transports the sample container holding the sample from the container mounting part to the ultrasonic vibrating unit.

17. The apparatus of claim 1, wherein
the sample preparation unit prepares the measurement sample by mixing the sample including the aggregated cells to which the ultrasonic vibration is applied, a RNase, and the fluorescence staining solution.

18. The apparatus of claim 1, further comprising a flow cytometer that measures fluorescence from a nucleus of a cell in the measurement sample prepared by the sample preparation unit.

19. A sample preparation apparatus comprising;
an ultrasonic vibrating unit which applies ultrasonic vibration to a sample including aggregated cells held in a sample container;
a sample preparation unit which prepares a measurement sample by mixing the sample including the aggregated cells to which the ultrasonic vibration is applied and a predetermined reagent;
a container transporting unit which transports the sample container holding the sample including the aggregated cells from the ultrasonic vibrating unit to the sample preparation unit;
a controller configured to control the container transporting unit to:
  raise the sample container at the ultrasonic vibrating unit to a first position above the ultrasonic vibrating unit;
  move the sample container from the first position to a second position above the sample preparation unit; and
  lower the sample container from the second position so as to set the sample container in the sample preparation unit; and
a liquid removing unit which removes a liquid attached to the sample container;
wherein the container transporting unit transports the sample container from the ultrasonic vibrating unit to the liquid removing unit and from the liquid removing unit to the sample preparation unit.

20. The apparatus of claim 19, wherein
the liquid removing unit includes a body having a holding concave portion which can hold at least portion immersed in the liquid in the sample container, an air supplying unit which supplies air to the outer periphery surface of the sample container held in the holding concave portion, and an air aspirating unit which aspirates the supplied air.

21. The apparatus of claim 20, wherein
the air supplying unit has a plurality of air supplying openings formed on the inner periphery surface of the holding concave portion in a circumferential direction.

* * * * *